(12) United States Patent
Kotha et al.

(10) Patent No.: US 10,526,616 B2
(45) Date of Patent: Jan. 7, 2020

(54) NANOPARTICLE-MEDIATED GENE DELIVERY, GENOMIC EDITING AND LIGAND-TARGETED MODIFICATION IN VARIOUS CELL POPULATIONS

(71) Applicant: RENSSELAER POLYTECHNIC INSTITUTE, Troy, NY (US)

(72) Inventors: Shiva Prasad Kotha, Mechanicville, NY (US); Andre Ronald Watson, Troy, NY (US); Vaibhav A. Pandit, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 15/024,264

(22) PCT Filed: Sep. 23, 2014

(86) PCT No.: PCT/US2014/057000
§ 371 (c)(1),
(2) Date: Mar. 23, 2016

(87) PCT Pub. No.: WO2015/042585
PCT Pub. Date: Mar. 26, 2015

(65) Prior Publication Data
US 2016/0230189 A1 Aug. 11, 2016

Related U.S. Application Data

(60) Provisional application No. 61/881,072, filed on Sep. 23, 2013.

(51) Int. Cl.
| | |
|---|---|
| C12N 15/85 | (2006.01) |
| C12N 15/88 | (2006.01) |
| A61K 47/64 | (2017.01) |
| A61K 47/69 | (2017.01) |
| A61K 48/00 | (2006.01) |
| C12N 9/22 | (2006.01) |

(52) U.S. Cl.
CPC .......... *C12N 15/85* (2013.01); *A61K 47/6455* (2017.08); *A61K 47/6923* (2017.08); *A61K 47/6929* (2017.08); *C12N 15/88* (2013.01); *A61K 48/0041* (2013.01); *C12N 9/22* (2013.01); *C12N 2800/95* (2013.01)

(58) Field of Classification Search
None
See application file for complete search history.

(56) References Cited

U.S. PATENT DOCUMENTS

| | | | |
|---|---|---|---|
| 6,376,248 B1 | 4/2002 | Hawley-Nelson et al. | |
| 6,379,966 B2 | 4/2002 | Monahan et al. | |
| 6,805,904 B2 | 10/2004 | Anders et al. | |
| 7,098,032 B2 | 8/2006 | Trubetskoy et al. | |
| 7,999,025 B2 | 8/2011 | Shumaker-Parry et al. | |
| 8,323,618 B2 | 12/2012 | Bikram | |
| 8,324,333 B2 | 12/2012 | Liu et al. | |
| 8,389,485 B2 | 3/2013 | Czech et al. | |
| 8,450,107 B1 | 5/2013 | Zhang et al. | |
| 9,315,788 B2* | 4/2016 | Duchateau ............ | C12N 9/16 |
| 2004/0067503 A1* | 4/2004 | Tan ................ | B82Y 15/00 |
| | | | 435/6.1 |
| 2004/0102606 A1 | 5/2004 | Balicki et al. | |
| 2005/0053668 A1 | 3/2005 | Vail | |
| 2006/0088599 A1 | 4/2006 | Prasad et al. | |
| 2007/0026069 A1 | 2/2007 | Shastri et al. | |
| 2007/0190155 A1 | 8/2007 | Leary et al. | |
| 2010/0015218 A1 | 1/2010 | Jadhav et al. | |
| 2010/0196492 A1 | 8/2010 | Green et al. | |
| 2010/0285111 A1 | 11/2010 | Ko et al. | |
| 2010/0311168 A1 | 12/2010 | Samuel et al. | |
| 2011/0145940 A1 | 6/2011 | Voytas et al. | |

(Continued)

FOREIGN PATENT DOCUMENTS

| | | |
|---|---|---|
| CN | 1662815 A | 8/2005 |
| CN | 102770539 A | 11/2012 |
| RU | 22950954 C2 | 3/2007 |

(Continued)

OTHER PUBLICATIONS

McNeer et al., Systemic Delivery of Triplex-forming PNA and Donor DNA by Nanoparticles Mediates Site-Specific Genome Editing of Human Hematopoietic Cells in Vivo, Gene Therapy (2013), Journal, Jun. 30, 2013, pp. 658-669, vol. 20, http://www.nature.com/gt/journal/v20/n6/abs/gt201282a.html.

(Continued)

*Primary Examiner* — James D Schultz
(74) *Attorney, Agent, or Firm* — Murtha Cullina LLP

(57) ABSTRACT

An improved nanoparticle for transfecting cells is provided. The nanoparticle includes a core polyplex and a silica coating on the core polyplex and, optionally, a polymer attached to an outer surface of the silica coating, where the polyplex includes an anionic polymer, a cationic polymer, a cationic polypeptide, and a polynucleotide. Also provided is an improved method of modifying intracellular polynucleotides. The method includes contacting a cell with a nanoparticle that includes a core polyplex and a silica coating on the core polyplex and, optionally, a polymer attached to an outer surface of the silica coating, where the polyplex includes an anionic polymer, a cationic polymer, a cationic polypeptide, and a polynucleotide.

23 Claims, 26 Drawing Sheets

Specification includes a Sequence Listing.

(56) References Cited

U.S. PATENT DOCUMENTS

2012/0244224 A1 9/2012 Biris et al.
2014/0005379 A1 1/2014 Gu

FOREIGN PATENT DOCUMENTS

| WO | 2005123142 | | 12/2005 |
|---|---|---|---|
| WO | 2011096408 | A1 | 8/2011 |
| WO | 2014093701 | | 6/2014 |

OTHER PUBLICATIONS

Ramakrishna et al., Gene Disruption by Cell-penetrating Peptide-mediated Delivery of Cas9 Protein and Guide RNA, Journal, Genome Res. 2014, Apr. 2, 2014, pp. 1-28, http://genome.cship.org/content/early/2014/04/02/gr.171264.113.

Lee et al, A Fabricated siRNA Nanoparticle for Ultralong Gene Silencing in Vivo, Advanced Functional Materials, vol. 23, Issue 28, Jul. 26, 2013, Journal, pp. 3488-3493, http://onlinelibrary.wiley.com/doi/10.1002/adfm.201202777/abstract;jsessionid=3C0867D99024D976B6337F5D185B9454.f02103.

McNeer et al., Nanoparticles Deliver Triplex-Forming PNA's for Site-Specific Genomic Recombination in CD34+ Human Hematopoietic Progenitors, Mol Ther. Jan. 2011;19(1), Journal, Jan. 31, 2011, pp. 172-180, http://nature.com/mtna/journal/v2/n11/full/mtna201359a.html.

Tyrrell et al., Multilayered Nanoparticles for Controlled Release of Paclitaxel Formed by Near-Critical Micellization of Triblock Copolymers, Marcomolecules 2012, vol. 45, Journal, Dec. 31, 2012, pp. 4809-4817, http://pubs.acs.org/doi/abs/10.102/ma300271k.

Chou et al., Strategies for the Intracellular Delivery of Nanoparticles, Chem Soc Rev 2011, vol. 40, Jan. 31, 2011, Journal, pp. 233-245,http://www.ncbi.nlm.nih.gov/pubmed/20886124.

International Search Report for PCT/US2014/057000 dated Jan. 14, 2015.

Miyata, et al, "Enhanced transfection with silica-coated polyplexes loading plasmid DNA," Biomaterials, Mar. 20, 2010, vol. 31, No. 17, pp. 4764-4770.

Wang, et al, "Influence of the polyanion on the physico-chemical properties and biological activities of polyanion/DNA/polycation ternary polyplexes," Acta Biomater, Apr. 27, 2012, vol. 8, No. 8, pp. 3014-3026.

Reilly, et al, "Histone H3 tail peptides and poly(ethylenimine) have synergistic effects for gene delivery," Mol Pharm., Apr. 25, 2012, vol. 9, No. 5, pp. 1031-1040.

Opanasopit, et al, "The development of poly-L-arginine-coated liposomes for gene delivery," Int J Nanomedicine, Oct. 7, 2011, vol. 6, pp. 2245-2252.

Watson, et al, "Optimizing Polymeric Nanoparticle Core Designs for Gene Delivery," Bioengineering Conference (NEBEC), 2013 39th Annual Northeast, Apr. 5-7, 2013, Syracuse, New York.

Douglas, et al, "Effects of alginate inclusion on the vector properties of chitosan-based nanoparticles," Journal of Controlled Release, 2006, vol. 115, pp. 354-361.

Peng, et al, "Mechanisms of cellular uptake and intracellular trafficking with chitosan/DNA/poly(y-glutamic acid) complexes as a gene delivery vector," Biomaterials, 2011, vol. 32, pp. 239-248.

Liao, et al, "Enhancement of efficiencies of the cellular uptake and gene silencing of chitosan/siRNA complexes via the inclusion of a negatively charged poly (y-glutamic acid)," Biomaterials, 2010, vol. 31, pp. 8780-8788.

Larsen, et al, "Using the Epigenetic Code to Promote the Unpackaging and Transcriptional Activation of DNA Polyplexes for Gene Delivery," Molecular Pharmaceutics, 2012, vol. 9, pp. 1041-1051.

Vaibhav Pandit et al; Multilayered Nanoparticles for Gene Delivery Used to Reprogram Human Foreskin Fibroblasts to Neurospheres, Tissue Engineering, Part C, vol. 21, No. 8, Apr. 17, 2015, pp. 786-794.

Vaibhav Pandit et al; Supplementary Data, Multilayered Nanoparticles for Gene Delivery Used to Reprogram Human Foreskin Fibroblasts to Neurospheres, Tissue Engineering, Part C, vol. 21, No. 8, Apr. 17, 2015, pp. 1-8.

European Search Report dated Apr. 18, 2017.

Watson, Andre, Tyler Denman, Vaibhav Pandit, Michael O'Neil, and Shiva P. Kotha. "Semi-stable Polymeric Nanoparticles as Genetic Vectors with Novel Release Kinetics." Biomedical Engineering Society Annual Meeting. Georgia World Congress Center, Atlanta. Oct. 27, 2012. Poster Presentation.

Douglas, Kimberly L., Ciriaco A. Piccirillo, and Maryam Tabrizian. "Effects of alginate inclusion on the vector properties of chitosan-based nanoparticles." Journal of controlled release 115.3 (2006): 354-361.

Liao, Zi-Xian, et al. "Enhancement of efficiencies of the cellular uptake and gene silencing of chitosan/siRNA complexes via the inclusion of a negatively charged poly (γ-glutamic acid)." Biomaterials 31.33 (2010): 8780-8788.

Tugyi, Regina, et al. "Partial D-amino acid substitution: Improved enzymatic stability and preserved Ab recognition of a MUC2 epitope peptide." Proceedings of the National Academy of Sciences of the United States of America 102.2 (2005): 413-418.

Chu, David SH, Russell N. Johnson, and Suzie H. Pun. "Cathepsin B-sensitive polymers for compartment-specific degradation and nucleic acid release." Journal of Controlled Release 157.3 (2012): 445-454.

Knowles, Richard G., et al. "Formation of nitric oxide from L-arginine in the central nervous system: a transduction mechanism for stimulation of the soluble guanylate cyclase." Proceedings of the National Academy of Sciences 86.13 (1989): 5159-5162.

Coradin, T., O. Durupthy, J. Livage "Interactions of amino-containing peptides with sodium silicate and colloidal silica: a biomimetic approach of silication." Langmuir 18 (2002): 2331-2336.

Abstract of Watson, Andre, Cara Yocum, Vaibhav Pandit, and Shiva P. Kotha. "Optimizing Polymeric Nanoparticle Core Designs for Gene Delivery: Design Layer by Layer." 2013 Northeast Bioengineering Conference. Syracuse University, New York. Apr. 6, 2013.

Watson, Andre, Cara Yocum, Vaibhav Pandit, and Shiva P. Kotha. "Optimizing Polymeric Nanoparticle Core Designs for Gene Delivery: Design Layer by Layer." 2013 Northeast Bioengineering Conference. Syracuse University, New York. Apr. 6, 2013.

Watson, Andre, Cara Yocum, Vaibhav Pandit, and Shiva P. Kotha. "Optimizing Polymeric Nanoparticle Core Designs for Gene Delivery: Design Layer by Layer." 2013 Northeast Bioengineering Conference. Syracuse University, New York. Apr. 6, 2013. Transcript of podium presentation.

* cited by examiner

FIGURE 8

NANOPARTICLE-MEDIATED GENE DELIVERY, GENOMIC EDITING AND LIGAND-TARGETED MODIFICATION IN VARIOUS CELL POPULATIONS

CROSS-REFERENCE TO RELATED APPLICATIONS

This application is a national stage filing under section 371 of International Application No. PCT/US2014/057000, filed on Sep. 23, 2014, and published in English on Mar. 26, 2015 as WO 2015/042585 A1, and claims priority under 35 U.S.C. § 119 to U.S. Provisional Application No. 61/881,072, filed Sep. 23, 2013, the entire disclosures of each of the prior applications are hereby incorporated herein by reference.

GOVERNMENT RIGHTS STATEMENT

This invention was made with U.S. Government support under R01 AG030637 awarded by the National Institutes of Health. The U.S. Government has certain rights in the invention.

BACKGROUND OF THE INVENTION

Technical Field

The present invention generally relates to use of nanoparticles to transfect cells. More particularly, the present invention relates to coated nanoparticles with a polyplex core for intracellular delivery of ploynucleotides to modify gene expression.

Background Information

Introducing polynucleotides into cells to alter gene expression requires appropriate packaging of the polynucleotides to protect them from degradation before cell entry, to permit entry into cells, and to direct delivery to the appropriate subcellular compartment. Effectiveness in altering expression may also depend on time-frames of release of polynucleotides from packaging after cellular entry. Available nanoparticle-based technologies for modifying gene expression suffer from low levels of cellular transfection and limited effectiveness upon transfection, at least in part because of their limitations in satisfying the foregoing requirements. It is therefore desirable to obtain a nanoparticle-based transfection agent and method of use thereof that addresses all of these requirements to enhance effectiveness.

SUMMARY OF THE INVENTION

The shortcomings of the prior art are overcome, and additional advantages are provided, through the provision, in one aspect, of a nanoparticle. The nanoparticle includes a core polyplex and a silica coating on the core polyplex, and the polyplex includes an anionic polymer, a cationic polymer, a cationic polypeptide, and a polynucleotide. In another aspect, the nanoparticle may also include a polymer attached to an outer surface of the silica coating.

A method of modifying intracellular polynucleotides is also provided. The method includes contacting a cell with a nanoparticle that includes a core polyplex and a silica coating on the core polyplex, and the polyplex includes an anionic polymer, a cationic polymer, a cationic polypeptide, and a polynucleotide. In another aspect, the nanoparticle may also include a polymer attached to an outer surface of the silica coating.

Additional features and advantages are realized through the techniques of the present invention. These, and other objects, features and advantages of this invention will become apparent from the following detailed description of the various aspects of the invention taken in conjunction with the accompanying drawings.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

FIG. 8 is photomicrographs of cells transfected with nanoparticles showing duration of residence of nanoparticles in cells following transfection in accordance with an aspect of the present invention;

DETAILED DESCRIPTION OF THE INVENTION

Figure 1A:
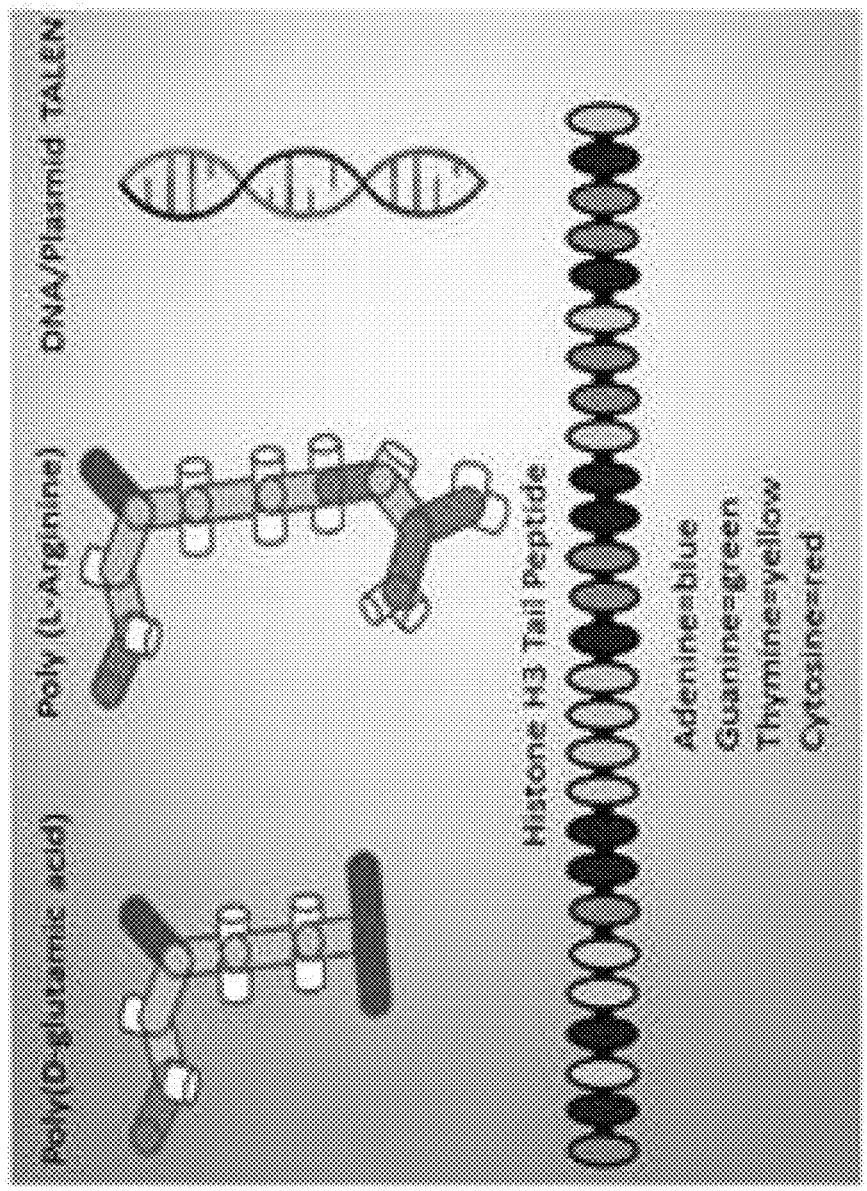
FIGS. 1A-1B are diagrammatic representations of some embodiments of a nanoparticle and components thereof in accordance with an aspect of the present invention.

Aspects of the present invention and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the invention in detail. It should be understood, however, that the detailed description and the specific examples, while indicating embodiments of the invention, are given by way of illustration only, and are not by way of limitation. Various substitutions, modifications, additions and/or arrangements within the spirit and/or scope of the underlying inventive concepts will be apparent to those skilled in the art from this disclosure.

The present disclosure provides, in part, a multilayered nanoparticle for transfecting cells with agents to modify gene expression. Nanoparticles designed for improved serum stability, targetted delivery to specific cell types, greater nuclear specificity and compartment-specific unpackaging, improved ability to retain significant payload levels during initial stages of internalization, and ability to maintain release of payload for a various durations following internalization, and methods of use thereof, are provided.

In one aspect, complexes of polynucleotides with polymers, or polyplexes, created by condensation of cationic polymers and polynucleotides in the presence of anionic polymers may mediate increased transfection efficiency over polynucleotide-cationic polymer conjugates. Though this process may produce more particles and increase the net surface area of nanoparticles exposed for cellular uptake, an improved electrostatic repulsory element may also be at play in releasing nucleic acids through this technique. Surprisingly, in contrast to a more rapid disaggregation of nucleotides from nanoparticle polyplexes that include anionic polymers as would have been predicted on the basis of existing literature, in one aspect of the present invention, including an anionic polymer in a nanoparticle polyplex core may prolong the duration of intracellular residence of the nanoparticle and release of agents that affect gene expression or otherwise regulate cellular function, or payloads.

In another aspect, the presence of a cationic polypeptide in a nanoparticle may mediate stability, subcellular compartmentalization, and payload release. As one example, fragments of the N-terminus of histone peptides, referred to generally as hi stone tail peptides, within various polyplexes are not only capable of being deprotonated by various histone modifications, such as in the case of histone acetyltransferase-mediated acetylation, but may also mediate effective nuclear-specific unpackaging as components of polyplexes. Their trafficking may be reliant on alternative endocytic pathways utilizing retrograde transport through the Golgi and endoplasmic reticulum, and the nature of histones existing inside of the nuclear envelope suggests an innate nuclear localization sequence on histone tail peptides. In one aspect of the present invention, including a histone tail peptide may promote nuclear localization of nanoparticles and result in enzyme-mediated release of polynucleotide payload therefrom.

In another aspect, silica coatings of polyplexes may seal their payloads before and during initial cellular uptake. Commonly used polyplexes consisting of poly(ethylenimine) and DNA have a tendency to shed the majority (~90%) of their payloads during cellular internalization, with the remaining payload often remaining bound to its cationic nanocarrier's polymeric remains. With transiently stabilizing interlayers of silica, greater intracellular delivery efficiency may be observed despite decreased probability of cellular uptake. In another aspect of the present invention, coating a nanoparticle polyplex with a silica coating may seal the polyplex, stablizing it until its release upon processing in the intended subcellular compartment.

In another aspect of the present invention, transfection efficiency may be further increased by adding another layer of cationic polymer, making the delivery efficiency as much as two orders of magnitude greater than a bare or silica-coated polyplex, presumably due to the anionic nature of an oligomeric silica coating being cell repulsive. In a further aspect, silica-coated polyplexes and their further-layered derivatives are stable in serum and are suitable for in vivo experiments unlike cationic polymer/nucleic acid conjugates on their own.

FIGS. 1A-1B show examples of components of a nanoparticle in accordance with the present invention. In accordance with the present invention, a nanoparticle polyplex core may include a polynucleotide, an anionic polymer, a cationic polymer, and a cationic polypeptide. A silica coating may then be applied to the polyplex core, and polymers may then be attached to an outer surface of the silica coating. The polynucleotide may be a DNA vector for driving intracellular expression of a nucleic acid sequence it contains. However, a nanoparticle may also comprise other types of polynucleotides, such as linear DNA or various types of RNA, including dsDNA, ssDNA, mRNA, siRNA, or CRISPR RNA sequences, or others, or any combination of the foregoing. A nanoparticle may also include, in addition to or in place of any of the foregoing examples of polynucleotides, a peptide nucleic acid, other charged or polar small molecules between 50 and 1000 Da, or alternatively between 200 and 10 kDa, in size, such as cyclic nucleotides such as cAMP, DNA origami templates, aptamers, charged polypeptides, proteins or protein fragments between 2 and 100 kDa, peptoids, phosphorylated or sulfated constituents, anionically modified constituents, and multimeric or oligomeric combinations of the foregoing. A person of ordinary skill would understand any of the foregoing, or any combination thereof, as being included within the present invention.

Continuing with FIG. 1A, in one aspect of the invention, a cationic polymer within the polyplex may be a polypeptide containing cationic amino acids and may be, for example, poly(arginine), poly(lysine), poly(histidine), poly(ornithine), poly(citrulline), or a polypeptide that comprises any combination of more than one of the foregoing. A nanoparticle may also include, in addition to or in place of any of the foregoing examples of cationic polymers, poly(ethylenimine), poly(aspartamide), polypeptoids, a charge-functionalized polyester, a cationic polysaccharide, an acetylated amino sugar, chitosan, or a variant or variants that comprise any combination of more than one of the foregoing, in linear or branched forms.

In one example, a cationic polymer may comprise a poly(arginine), such as poly(L-arginine). A cationic polymer within the polyplex may have a molecular weight of between 1 kDa and 200 kDa. A cationic polymer within the polyplex may also have a molecular weight of between 10 kDa and 100 kDa. A cationic polymer within the polyplex may also have a molecular weight of between 15 kDa and 50 kDa. In one example, a cationic polymer comprises poly(L-arginine) with a molecular weight of approximately 29 kDa, as represented by SEQ ID NO: 1 (PLR). In another example, a cationic polymer may comprise linear poly(ethylenimine) with a molecular weight of 25 kDa (PEI). In another example, a cationic polymer may comprise branched poly(ethylenimine) with molecular weight of 10 kDa. In another example, a cationic polymer may comprise branched poly(ethylenimine) with a molecular weight of 70 kDa. In another example, a cationic polymer may comprise a D-isomer of poly(arginine) or of any of the foregoing polymers such as polypeptides, which may be particularly advantageous because polymers such as polypeptides containing a D-isomer may be less susceptible to degradation within a cell and therefore have a prolonged effect on influencing payload release and the rate thereof over time.

Continuing with FIG. 1A, in a further aspect of the invention, an anionic polymer within the polyplex may be a polypeptide containing anionic amino acids, and may be, for example, poly-glutamic acid or poly-aspartic acid, or a polypeptide that comprises any combination of the foregoing. A nanoparticle may also include, in addition to or in place of any of the foregoing examples of anionic polymers, a glycosaminoglycan, a glycoprotein, a polysaccharide, poly(mannuronic acid), poly(guluronic acid), heparin, heparin sulfate, chondroitin, chondroitin sulfate, keratan, keratan sulfate, aggrecan, poly(glucosamine), or an anionic polymer that comprises any combination of the foregoing. In one example, an anionic polymer may comprise poly-glutamic acid. An anionic polymer within the polyplex may have a molecular weight of between 1 kDa and 200 kDa. An anionic polymer within the polyplex may also have a molecular weight of between 10 kDa and 100 kDa. An anionic polymer within the polyplex may also have a molecular weight of between 15 kDa and 50 kDa. In one example, an anionic polymer is poly(glutamic acid) with a molecular weight of approximately 15 kDa. Polymers consisting of or including a D-isomer of glutamic acid may be particularly advantageous because they may be less susceptible to degradation within a cell and therefore have a prolonged effect on influencing payload release and the rate thereof over time. For example, the anionic polymer within the polyplex may have the sequence represented by SEQ ID NO: 2 (PDGA). In another example, an anionic polymer may comprise a D-isomer of any of the foregoing polymers or polypeptides, which may be particularly advantageous because polymers such as polypeptides containing a D-isomer may be less susceptible to degradation within a cell and therefore have a prolonged effect on influencing payload release and the rate thereof over time.

Continuing with FIG. 1A, in another aspect of the invention, a cationic peptide in a nanoparticle's polyplex core may be a fragment of a histone peptide, such as of the H1, H2, H3, or H4 proteins. The fragment may include amino acids whose sequence corresponds to the N-terminus of a histone protein. For example, the fragment may comprise up to the first 5 (SEQ ID NO: 9), 10 (SEQ ID NO: 10), 15 (SEQ ID NO: 11), 20 (SEQ ID NO 12), 25 (SEQ ID NO: 13) or more N-terminal amino acids of a histone protein. The fragment may also be amidated on its C-terminus. The fragment may also have been modified such that one or more lysine residue is methylated, one or more histidine, lysine, arginine, or other complementary residues are acetylated or susceptible to acetylation as a histone acetyltransferase or acetyl CoA substrate, or any combination of the foregoing. For example, a cationic peptide in a nanoparticle polyplex core may have the sequence as represented by SEQ ID NO: 3, which comprises the first 25 amino acids of the human histone 3 protein, amidated on its C-terminus, and tri-methylated on the lysine 4 in accordance with the present invention (HTP).

In another embodiment, a nanoparticle may include or contain, in addition to or in place of any of the foregoing cationic polypeptides, a nuclear localization sequence. A cationic polypeptide may comprise a nuclear localization sequence on its N- or C-terminus. A nuclear localization sequence may comprise an importin or karyopherin substrate, or may have or contain a sequence corresponding to SEQ ID NO: 8. In another embodiment, a nanoparticle may include, in addition to or in place of any of the foregoing cationic polypeptides, a mitochondrial localization signal or a peptide fragment of mtHSP70.

Figure 1B:
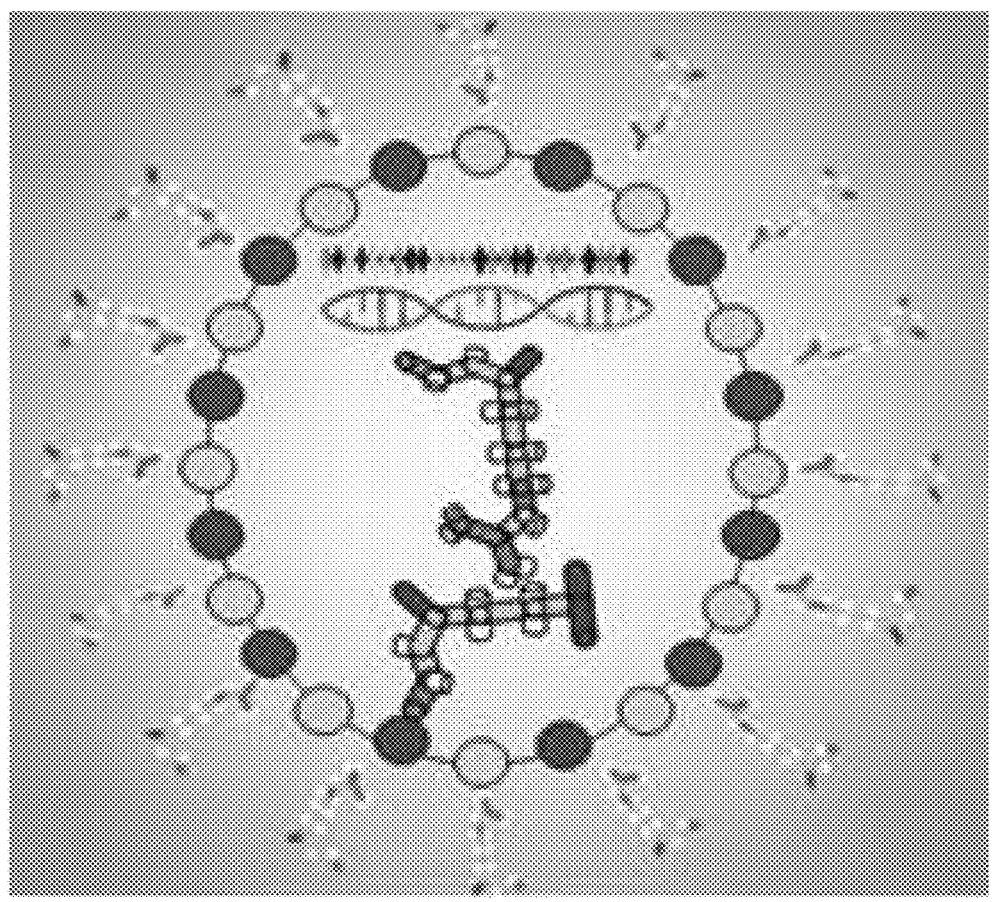

Continuing with FIG. 1B, in another aspect of the invention, the nanoparticle may comprise a reversible coating that provides stability to the polyplex core prior to cellular or compartmental internalization, preventing premature degradation or destabilization. For example, a silica coating may be applied to the polyplex core. In another example, calcium phosphate or hydroxyapatite may be applied to a polyplex core. In another example, a branched cationic polymer, polypeptide, or peptoid may be applied to a polyplex core, with an anionic charge excess. A coating, such as a silica coating, may protect the polyplex from degradation before exposure to the endosomal microenvironment.

In another aspect, a nanoparticle may comprise a layer of polymers attached to or electrostatically bound with the external surface of coated polyplex, such as to or with the external surface of a silica coating. Such external polymers may serve to prevent cellular repulsion of the coated polyplex so as to promote contact with and uptake by a cell. An external polymer layer may also serve to promote internalization by specific cell types, such as if the externally attached polymer is or mimics a ligand to a receptor expressed by a cell type of which transfection is desired. A polymer in a polymer layer attached to the outer surface of coating on a polyplex may be from between 0.1 to 20 kDa in size, or may be up to 40 or 50 kDa in size.

Examples of polymer comprising a polymer layer attached to the external surface of the coated core polyplex include those represented by SEQ ID NO: 4, which is an approximately 10 kDa poly(arginine) polymer, and SEQ ID NO: 5, which is human vasoactive endothelial growth factor protein, in accordance with the present invention. In another example, a polymer comprising a layer attached to the external surface of the coated core polyplex may comprise an anchor substrate of from between 1 to 25 repeating anionic or cationic moieties at the N-terminus, C-terminus, 5', or 3' end of a polymer, polypeptide, or polynucleotide to provide electrostatic conjugation of a targeting motif contained in the polymer, polypeptide, or polynucleotide to the coated polyplex core. In another example, a polymer comprising a layer attached to the external surface of the coated core polyplex may comprise a polymer, polypeptide, or polynucleotide sequence that exhibits base pair complementarity or binding affinity for an amino acid sequence binding motif to bind additional layers that may be added thereupon.

Figure 2A:
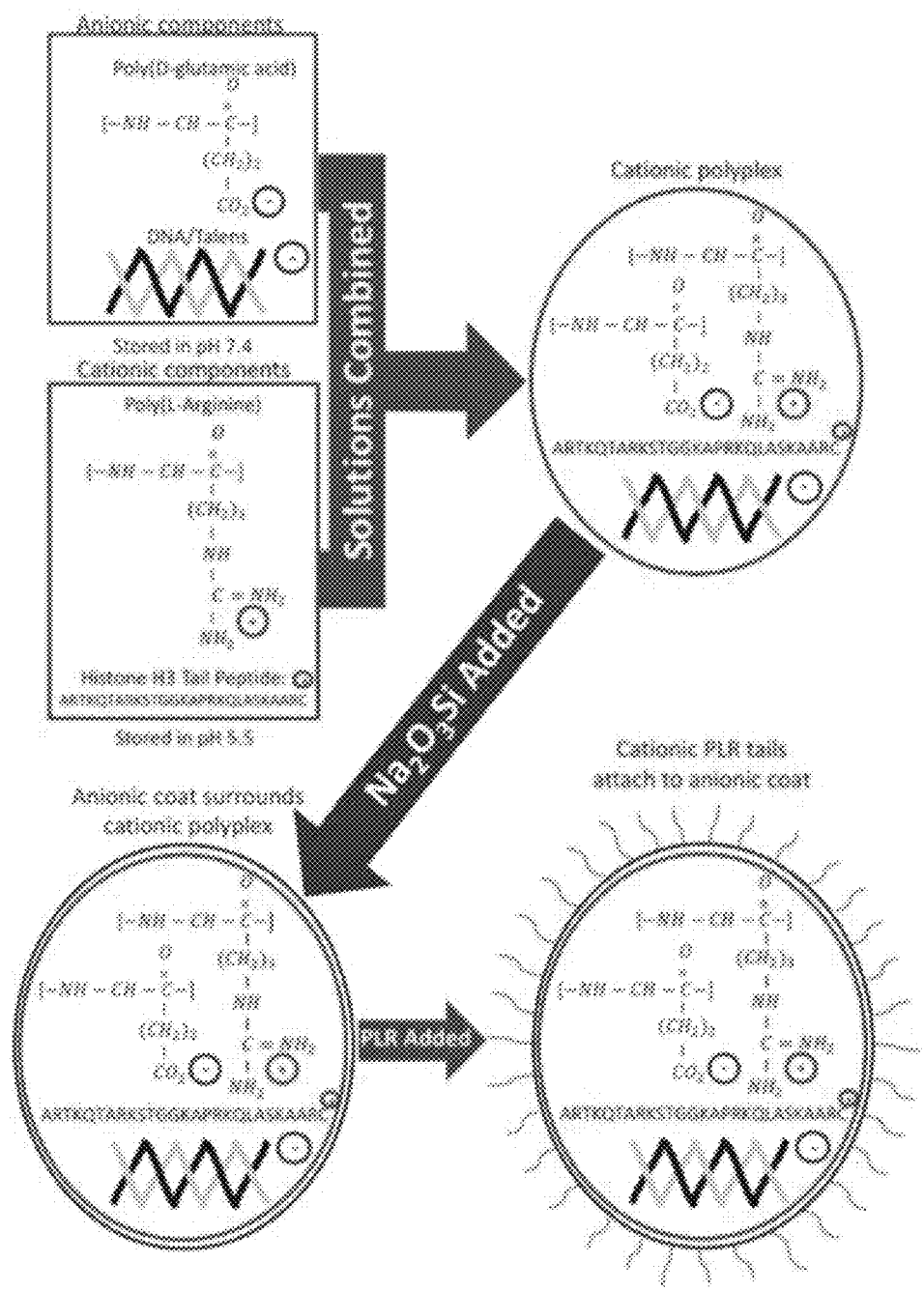
FIG. 2A is a diagrammatic representation of how a nanoparticle may be manufactured in accordance with an aspect of the present invention.

In another aspect of the present invention, illustrated in FIG. 2A, a cationic polyplex is created, then coated with a silica coating. Polyplex cores of nanoparticles may be created via electrostatic interactions leading to condensation. Two equal-volume solutions may be created, one with pH-unadjusted 40 mM HEPES (pH ~5.5) combined with 0.1% w/v a cationic polymer and a cationic polypeptide in water and the other with 30 mM Tris-HCl (pH ~7.4) combined with 0.1% w/v anionic polymers and a polynucleotide in water. In one embodiment, the cationic polymer comprises SEQ ID NO: 1, the anionic polymer comprises SEQ ID NO: 2, and the cationic polypeptide comprises SEQ ID NO: 3. These solutions may be combined via dropwise addition of the cationic solution to the anionic one with no stirring. After 30 minutes of incubation at room temperature, a 200 uL solution containing 10 ug of nucleic acids within polyplexes may be added dropwise to a 45 mM sodium silicate (Sigma) solution in Tris-HCl (pH=7.4) and allowed to incubate for between 8 and 24 hours at room temperature. Silica-coated polyplexes may be isolated via centrifugation with a 300 kDa Nanosep® filter (Pall, Port Washington, NY) at 3000g in order to isolate complexes from unbound silica species and polymers. Nanoparticles may further be resuspended in a solution containing a polymer to be attached to the external surface of the silica coating. For example, they may be resuspended in a solution comprising a polymer represented by SEQ ID NO: 4 or SEQ ID NO: 5 at 0.1% w/v for one hour. Nanoparticles may then be centrifuged again before resuspension in transfection medium. This method is but one example of manufacturing nanoparticles in accordance with the present invention.

Figure 2B:
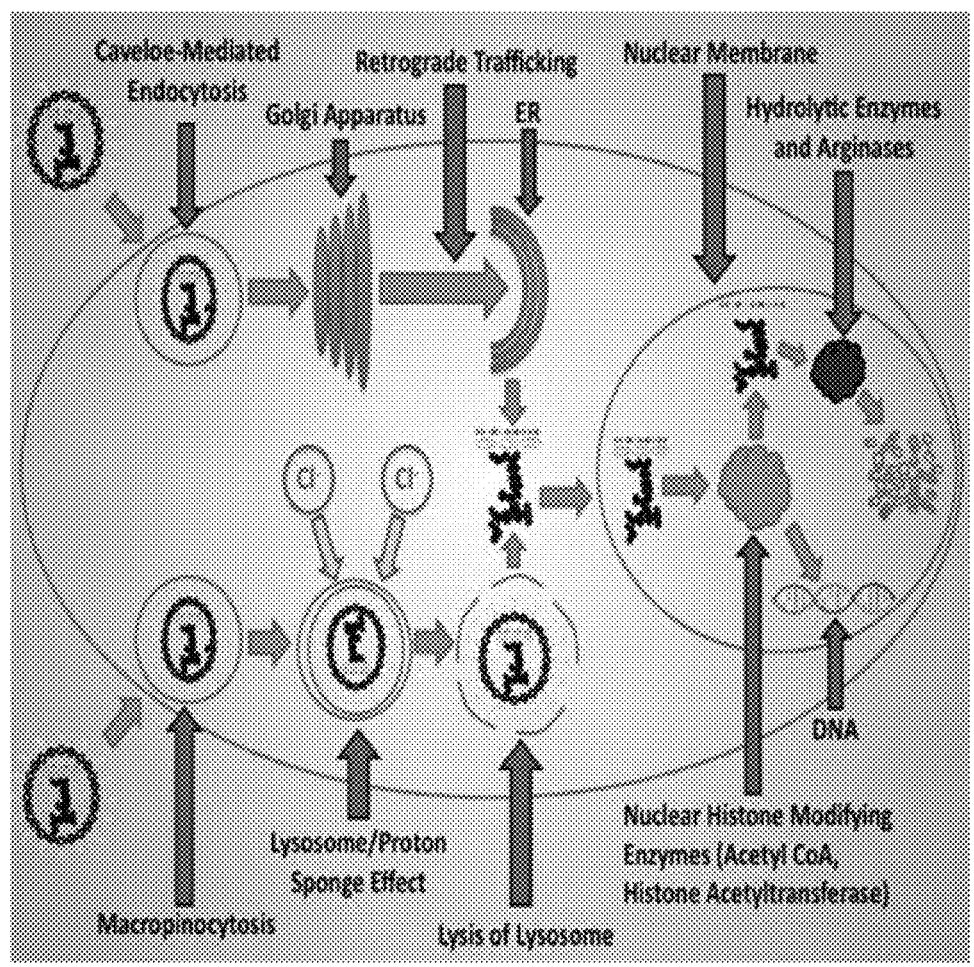
FIG. 2B is a diagrammatic representation of means by which a cell may uptake and intracellularly process a nanoparticle in accordance with an aspect of the present invention.

FIG. 2B is a diagrammatic representation of contacting a cell with a nanoparticle in accordance with the present invention leading to cellular internalization of the nanoparticle, such as by caveolae-mediated endocytosis or macropinocytosis. Nanoparticles may further be retrogradely transported through the Golgi and endoplasmic reticulum or processed through lysosomal pathways, resulting in loss of the coating, such as a silica coating, and exposure of the polyplex core. The polyplex core may further be translocated into the cell nucleus, where enzymatic processing my degrade the cationic polymer, such as through activity of arginases, or otherwise promote unpackaging of the polyplex core, such as through acetylation of a histone tail peptide within the polyplex, leading to release of polynucleotides such as plasmid DNA from the polyplex core, in accordance with the present invention. Other intracellular processing steps modifying the constituents of a nanoparticle and its polyplex core or coating thereof or polymer layer attached to the coating may also occur in accordance with the present invention.

In a further aspect, the present invention includes optimized ratios of anionic and cationic polymers, cationic polypeptides, and polynucleotides for complexation of a polyplex core as part of a nanoparticle. In one example, plasmid DNA was fluorescently tagged with ethidium bromide (40 ng EtBr/ug DNA) before addition of various polymeric constituents in molar [1(positive)]:[1(negative)] ratios of [amine (n)]:[phosphate (p)+carboxylate (c)], or of c:p in the instance of poly(D-glutamic acid) (PDGA; SEQ ID NO: 2) addition. Addition of linear poly(ethylenimine) (PEI, 25 kDa) was compared to addition of poly(L-arginine) (PLR, 29 kDa; SEQ ID NO: 1) independently, as well as in conjunction with a H3K4(Me3) histone tail peptide (HTP; SEQ ID NO: 3), in order to quantify similar complexation behaviors between the two polymers as part of a binary complex (i.e., PEI+DNA or PEI+DNA) or ternary complexes (HTP+PEI+DNA or HTP+PLR+DNA). Where a cationic polymer and cationic polypeptide were both present, the relative molar ratio of each component was 60%:40%, respectively. A Zeiss filter and spectrophotometer were used to excite EtBr-tagged DNA at 510 nm for an emission at 595 nm, and results were compared amongst various formulations with unbound EtBr as a negative control.

Figure 3:
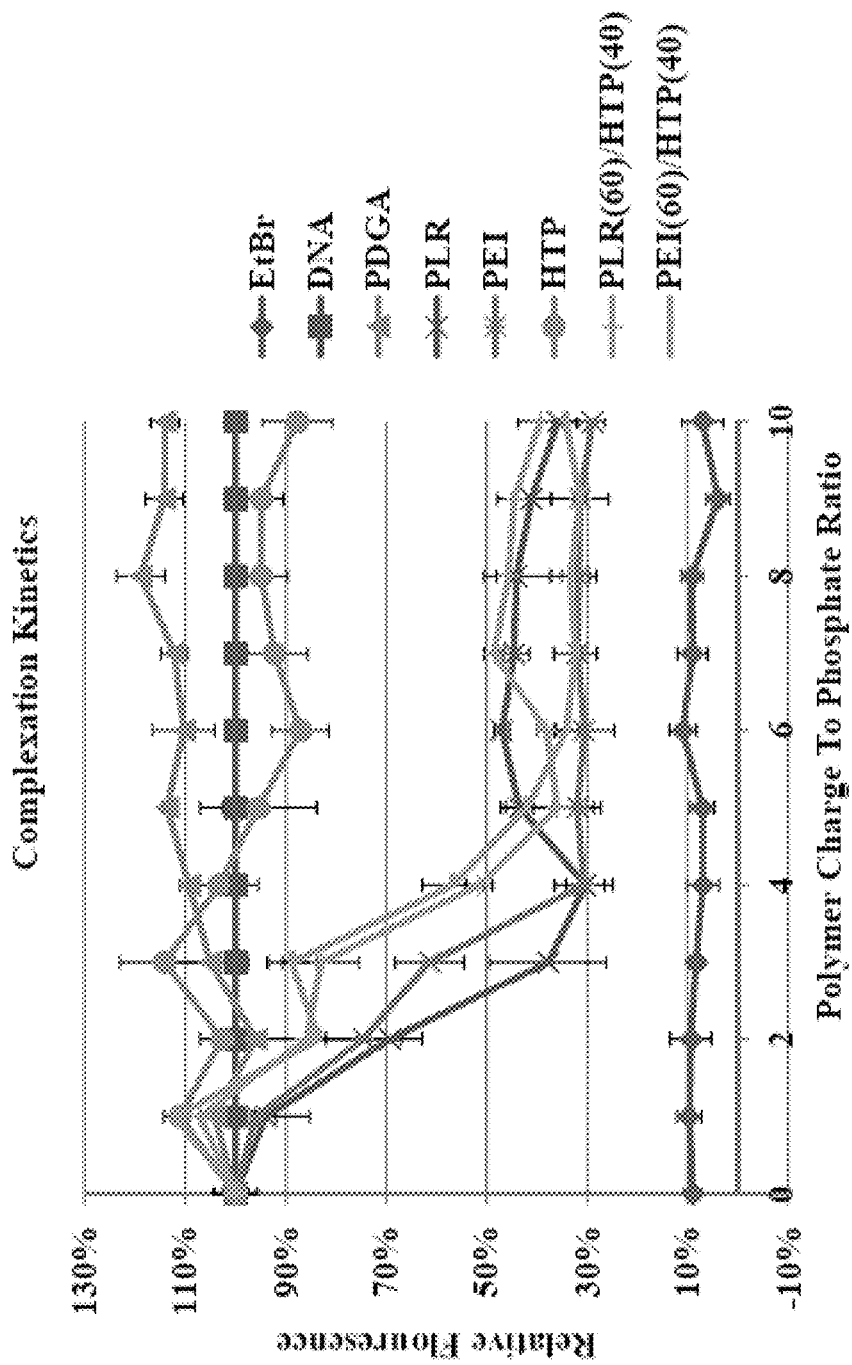
FIG. 3 is a graph illustrating the effects on polyplex complexation of including different ratios of various charged polymers and polynucleotides in accordance with an aspect of the present invention.

FIG. 3 is a graph showing the effects of varying the ratio of anionic or cationic polymers or polypeptides to polynucleotides. The X axis shows charged polymer-to-phosphate ratio and the Y axis shows relative fluorescence following combination of indicated constituents. A decrease in relative fluorescence indicates displacement of EtBr from DNA and polyplex formation. Ratios of cationic polymer, or of cationic polymer and cationic polypeptide, to DNA of approximately 5:1 and higher exhibited an approximately 40% decrease in fluorescence indicating complexation of DNA and polymers into polyplexes. Addition of PDGA in the absence of cationic polymers or cationic polypeptides did not affect complexation.

After complexing PLR-HTP-DNA, PEI-HTP-DNA, PLR-DNA and PEI-DNA polyplexes and determining that PDGA possesses no ability to cause complexation of polynucleotides, PDGA's influence on formation kinetics was established by comparison of [5.5(positive)]:[1(negative)] and [10(positive)]:[1(negative)] molar ratios of [amine (n)]: [phosphate (p)] and [amine (n)]:[phosphate (p)+carboxylate (c)] on complexation efficiencies in order to determine effects of excess cationic and equalized charge ratios on nanoparticle complexation. Inclusion of carboxylate groups from PDGA was expected to have effects on overall formation kinetics comparable to inclusion of phosphate groups from DNA. Relative fluorescence was compared to DNA without addition of polymers or polypeptides or EtBr in the absence of DNA as controls.

Figure 4:
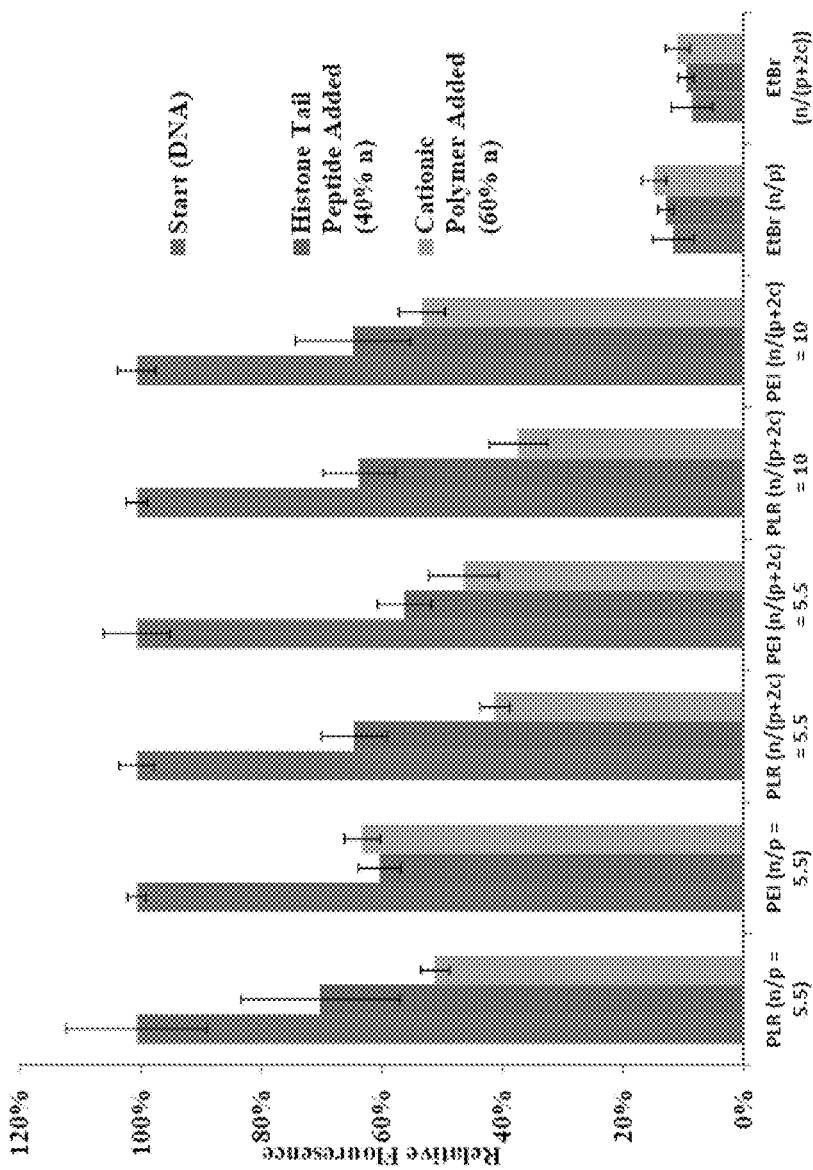
FIG. 4 is a graph illustrating the effects on polyplex complexation of including different ratios of various charged polymers and polynucleotides, with or without including an anionic polymer in the polyplex, in accordance with an aspect of the present invention.

FIG. 4 indicates the effects of adding PDGA to cationic polymers and cationic polypeptides on polyplex complexation kinetics. DNA was complexed with HTP, PLR or PEI, with or without addition of PDGA. Shown are experiments using cationic polymer (PLR or PEI)-to-polynucleotide molar ratios of 5.5:1 (as shown in the bars labeled n/p=5.5) and cationic polymer (PLR or PEI)-to-polynucleotide plus anionic polymer molar ratios of 5.5:1 and 10:1 (as shown in the bars labeled n/(p+2c)=5.5 or 10), with or without addition of HTP. Addition of PDGA did not impair complexation kinetics at any of the molar ratios tested.

Figure 5:
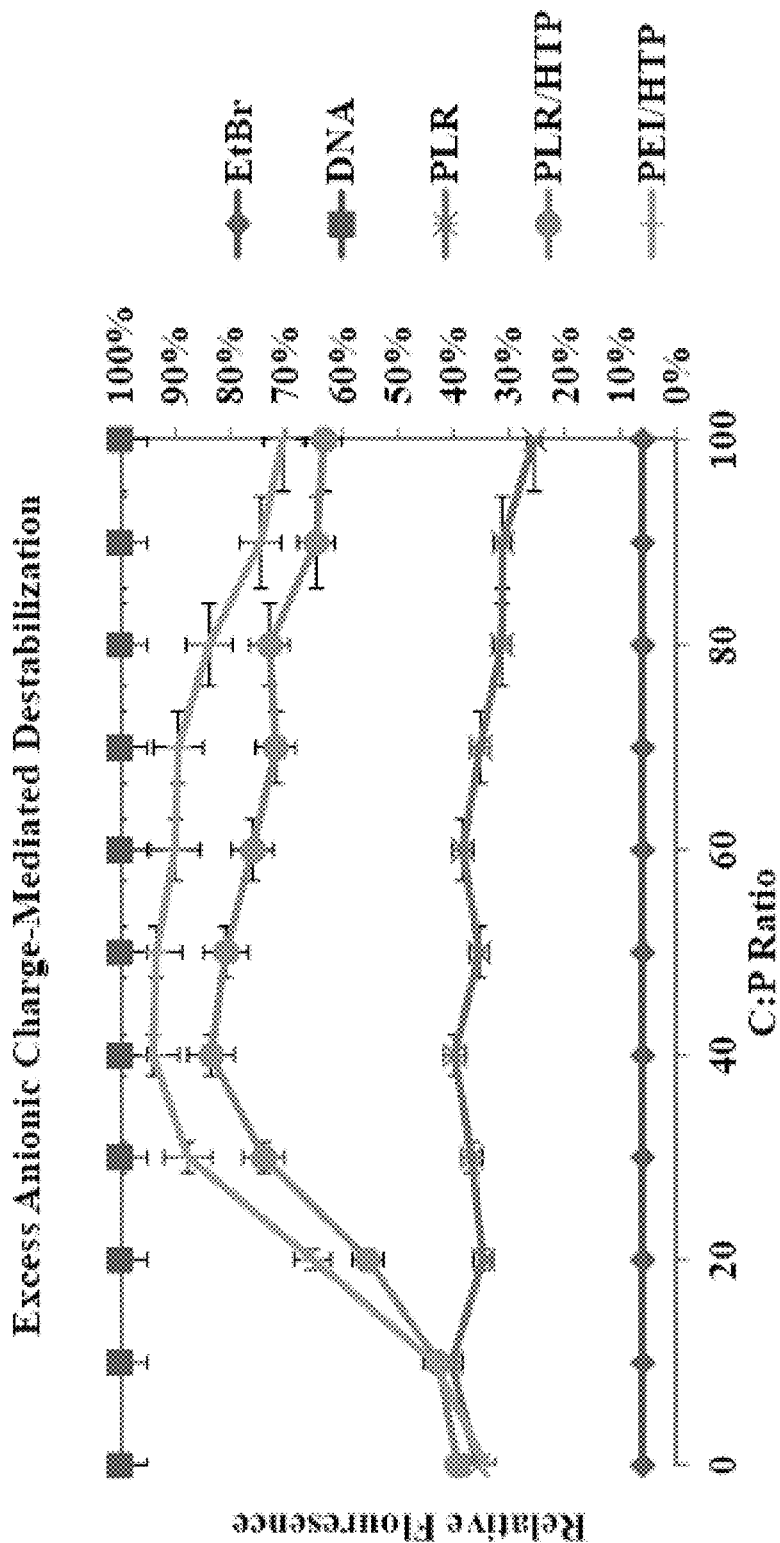
FIG. 5 is a graph illustrating the destabilizing effect on a polyplex of including increasing amounts of an anionic polymer in the presence or absence of cationic polypeptides in accordance with an aspect of the present invention.

Effects of including a cationic polymer and cationic polypeptide on polyplex destabilization were also determined, as shown in FIG. 5. Polyplex nanoparticles of DNA and cationic polypeptides (PLR with or without HTP, or PEI with HTP) with [(PDGA) carboxylate(c):(DNA) phosphate (p)] molar ratios varying from 0 to 100 were complexed as described, compared to DNA or EtBr alone as controls, and the effects of destabilization (as indicated by increased fluorescence) was determined. In the absence of HTP, addition of PDGA did not lead to polyplex destabilization. However, in the presence of HTP, adding molar ratios of PDGA to DNA of 20 and above led to polyplex destabilization. These results indicate a surprising synergistic effect of cationic polypeptide and anionic polymer on complex destabilization. Cationic polypeptide incorporation, and/or inclusion of cationic constituents of disparate molecular weights or sizes, into a nanoparticle polyplex core may beneficially enhance the ability of a cationic polymer to promote dissociation and release of the polynucleotide payload from the polyplex and its other constituents.

Figure 6:
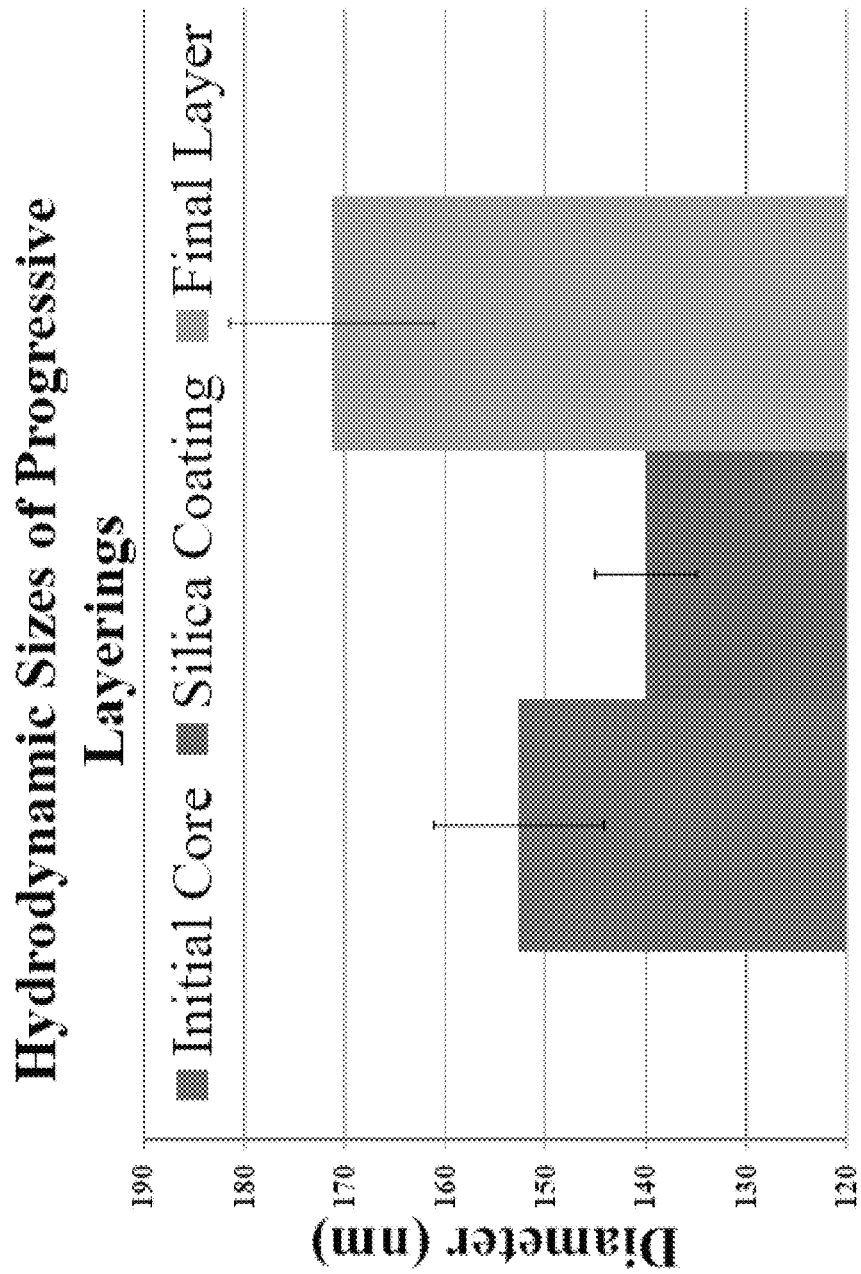
FIG. 6 is a graph illustrating sizes of nanoparticles possessing various layers in accordance with an aspect of the present invention.

Dynamic light scattering (BRAND) was used to determine the hydrodynamic radii of nanoparticles at various stages of formation. Nanoparticles containing core polyplexes with plasmid DNA, PLR, PDGA, and HTP, at a molar ratio of [amide]:[(phosphate)] of 5.5:1 were complexed as described. Some polyplex cores were further coated with silica as described. And some silica-coated polyplexes were further layered with cationic polymer (SEQ ID NO: 4) as described. 30-60 minutes of measurements were obtained following initial core formation of ternary complexes, silica coating of cores, and cationic polymer-coating of silica-coated cores. FIG. 6 is a graph showing diameters of nanoparticles. Uncoated polyplex cores and polyplex cores coated with silica were approximately 70-150 nm in diameter on average. In other embodiments, polyplex cores and silica-coated polyplex cores may be within a range of 100-170 nm in average diameter. Adding a cationic polymer coating to the silica coating yielded a nanoparticle with an average diameter of approximately 170 nm. In other embodiments, silica-coated polyplex cores with an additional layer of cationic polymer attached to the outer layer of silica may be within a range of approximately 80-200 nm in average diameter.

Cellular uptake of nanoparticles was also determined. Fluorescein isothiocyanate (FITC) was covalently conjugated to amines of PEI (25 kDa linear) and PLR (29 kDa) such that the molar ratio of amines to FITC was 100:1. The reaction was performed in darkness at room temperature for four hours in equal volumes of water and DMSO. In order to establish conjugation, a 0.05% w/v 500 uL solution of each fluorescently modified polymer was centrifuged in a 10 kDa Nanosep® filter and the eluate's fluorescence intensity (485 ex./520 em.) was compared to the unfiltered polymer solution as well as water. mCherry plasmid (Addgene) was included in nanoparticles to permit fluorescent detection of plasmid-driven expression.

MC3T3 murine osteoblasts were cultured on polystyrene T-75 tissue culture plastic flasks (Corning, CA, USA). Dulbecco's modified eagle medium supplemented with 10% Fetal Bovine Serum (Thermo Fisher Scientific, VA, USA) was used for osteoblasts along with 1% penicillin/streptomycin (Invitrogen, NY, USA). Xylenol orange was added to the cell culture media from day 15 to day 25 after initiation of cell culture. At day 25 cells were fixed and assayed for mineralization. For mCherry plasmid delivery using FITC-modified nanoparticles, osteoblasts were plated at 1000 cells/well in 96-well plates and allowed to adhere for 12-16 hours in antibiotic-free DMEM containing 10% FBS. Immediately before transfection, medium was replaced with equal volumes of OptiMEM-suspended nanoparticles and DMEM containing 10% FBS.

All complexes were FITC-labeled and subjected to qualitative observation of fluorescence intensity (488/520 ex./em.) before transfection. 96-well-plated osteoblasts (1000 cells/well) were transfected with 200 ng of plasmids in triplicates for each binary (plasmid and cationic polymer), ternary (plasmid and cationic polymer, plus anionic polymer or cationic polypeptide), and quaternary (plasmid, cationic polymer, anionic polymer, and cationic polypeptide) complex as well as its silica-coated counterpart, with 1 control and 8 experimental sets (n=3) in total. 5% serum was used in order to study effects of serum on extracellular properties of aggregation.

At 30-hours post-transfection, bimodal fluorescent imaging allowed for simultaneous observation of FITC-labeled nanoparticles (488 ex./520 em.) and the mCherry gene expression that they were responsible for (633 ex./680 em.). A minimum of 20 cells were observed at different locations in each well and representative images were obtained. ImageJ was used to process the overlaid images and combine phase-contrast, 488/520 and 633/680 channels.

Figure 7:
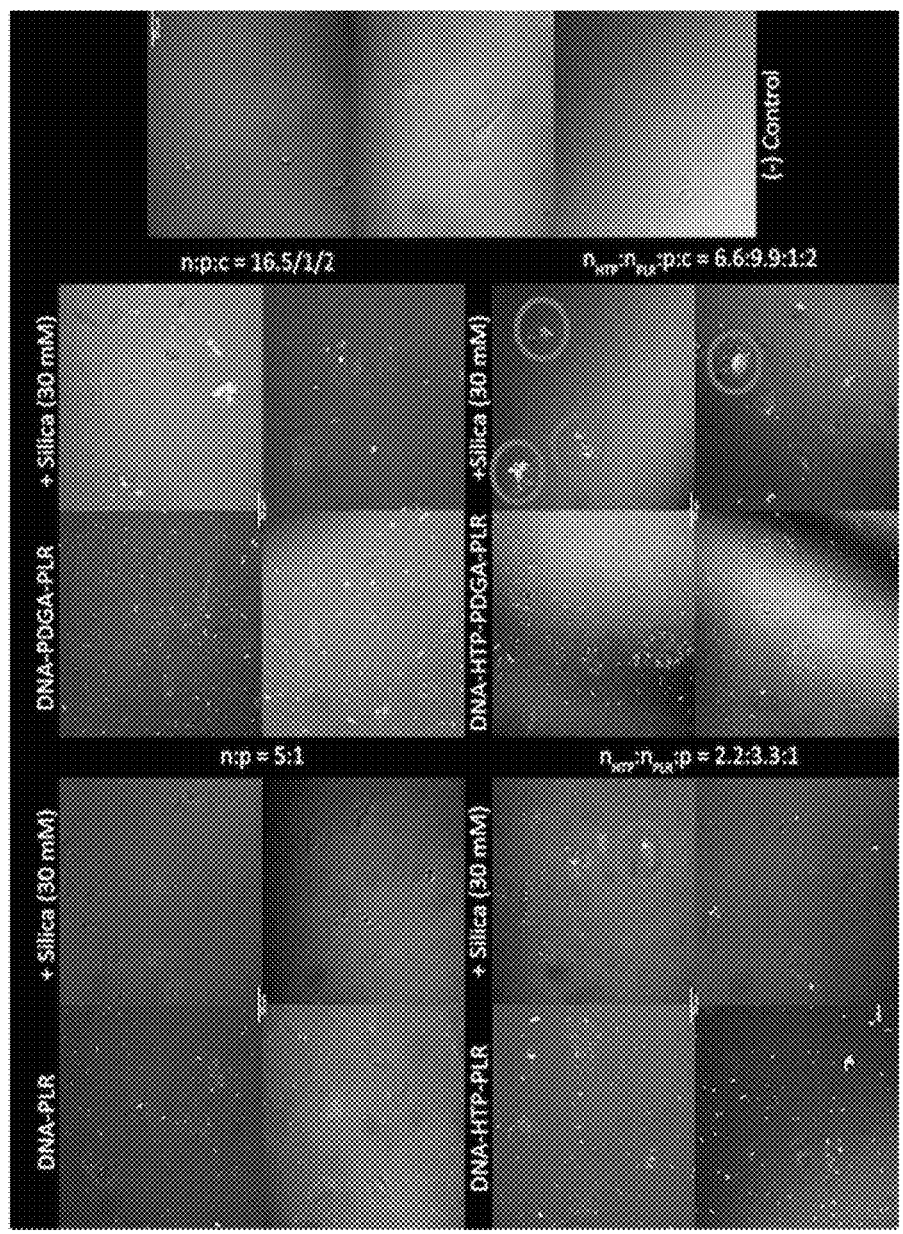
FIG. 7 is photomicrographs of cells transfected with various nanoparticles demonstrating cellular uptake and subcellular localization of nanoparticles following transfection in accordance with an aspect of the present invention.

Photomicrographs demonstrating cellular uptake are shown in FIG. 7. Circles in FIG. 7 indicate where high levels of nuclear localization is apparent. Silica-coated binary nanoparticles show burst release properties (i.e., nuclear localization is not apparent in the DNA-PLR+silica samples). Inclusion of PDGA in polyplex cores causes prolonged release of plasmid within cell nuclei. This effect of PDGA to cause prolonged release was surprising in light of literature suggesting the opposite: that including cationic polymers in nanoparticle polyplexes would hasten, and shorten the duration of, dissociation of polynucleotide payload from other polyplex constituents. Addition of HTP also causes extensive nuclear localization.

Figure 8:
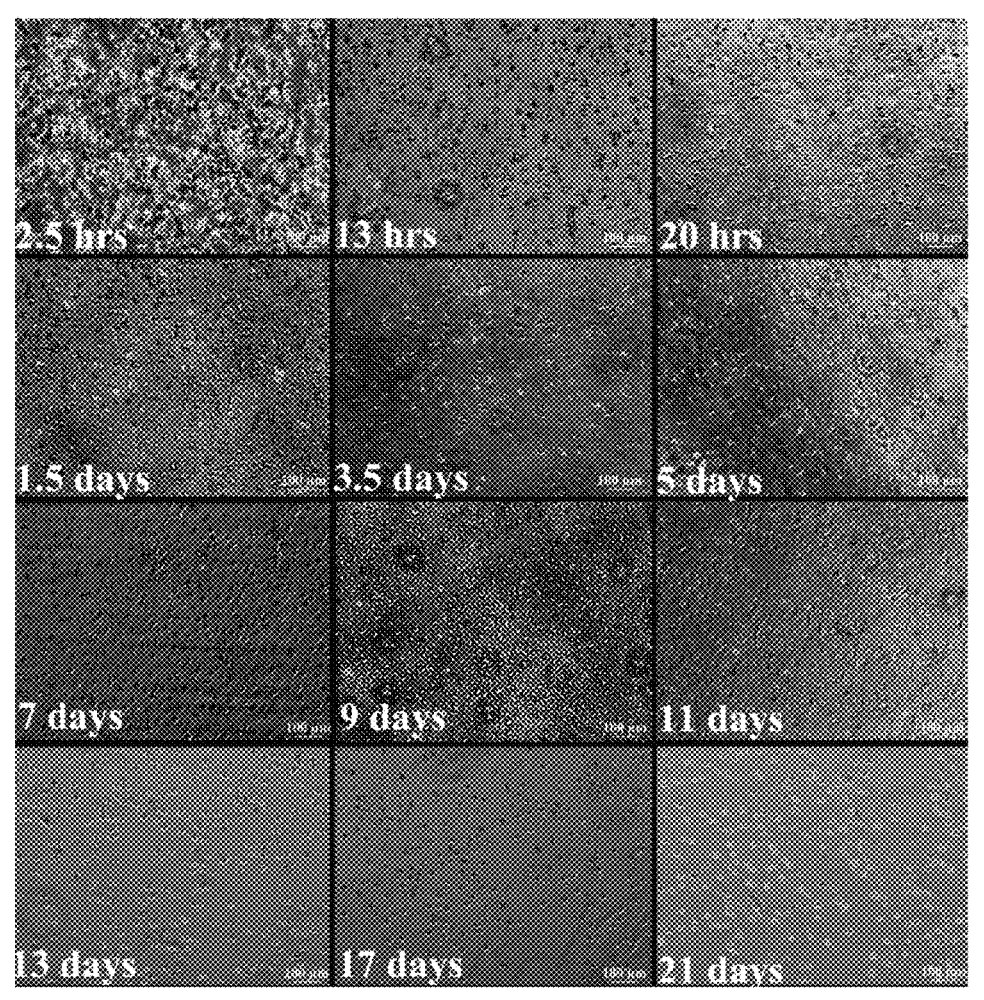

Further coating of silica-coated nanoparticles (DNA-HTP-PDGA-PLR+Si) with poly(arginine) (SEQ ID NO: 4) causes nanoparticles to be stable in serum and causes extended residence of nanoparticle payload within cells. FIG. 8. is photomicrographs showing cellular uptake and retention of silica-coated FITC-conjugated polyplex cores, to which an additional layer of poly(L-arginine) (SEQ ID NO: 4) has been added, by MC3T3 murine osteoblasts, in accordance with the present invention. Unlike for silica-coated nanoparticles shown in FIG. 7, no aggregation of nanoparticles containing an additional layer of cationic polymers on the outside of the silica coating is observable in FIG. 8, indicating that such nanoparticles remain stable in serum. Furthermore, these nanoparticles are observed to display extended residence within the cell nucleus such that fluorescence qualitatively peaks within approximately 1.5 days and detectable fluorescence was sustained through 14 days.

Figure 9A:
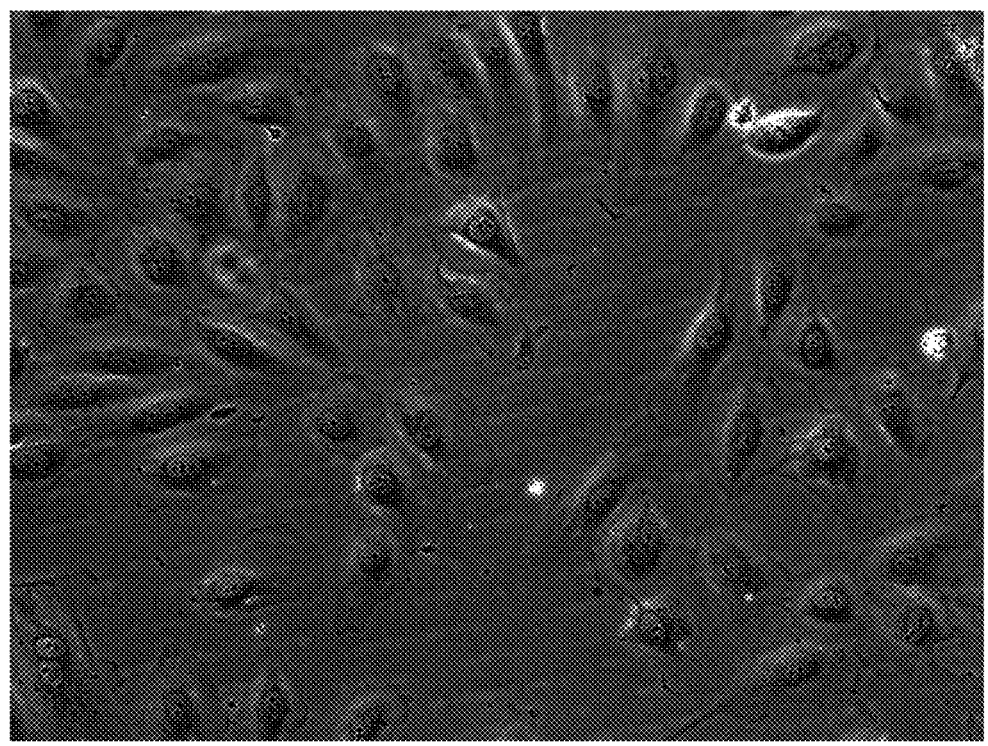
FIGS. 9A-B is photomicrographs showing cellular uptake of nanoparticles possessing a layer of polymers attached to the outside of a silica coating of a polyplex in accordance with an aspect of the present invention.
Figure 9B:
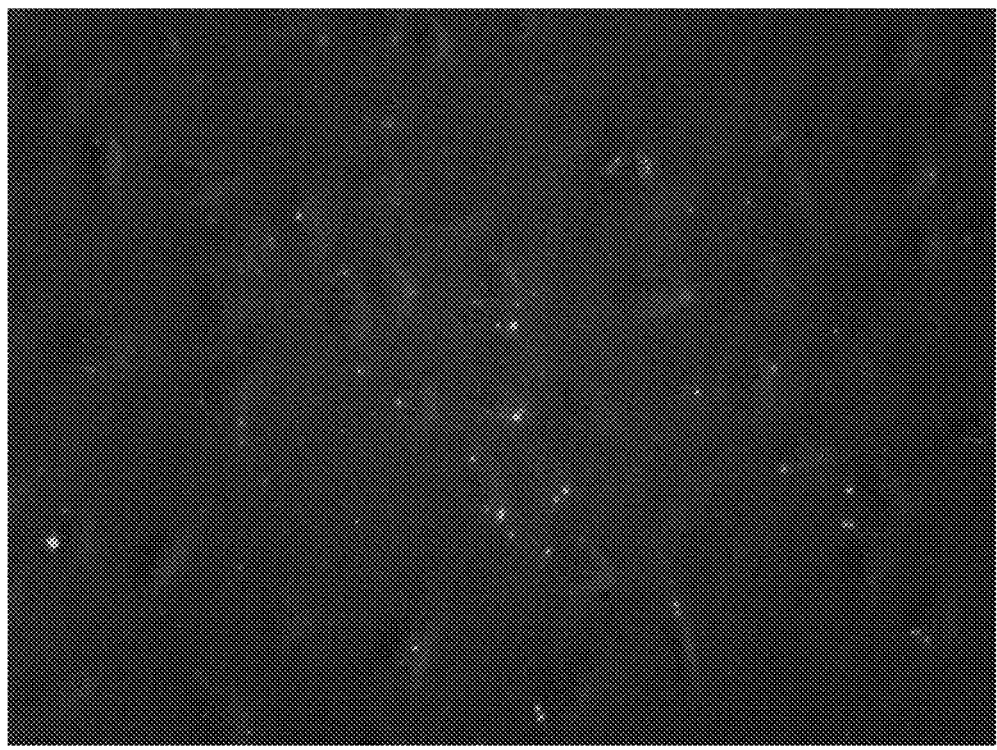

Layering silica-coated polyplex cores with polymers specifically directed to bind to particular cell types can further enhance uptake. Associating ligands for cellular receptors with the surface of a nanoparticle can enhance affinity of the nanoparticle for cells that express such receptors and increase transfection of such cells. As one example in accordance with the present invention, silica-coated polyplexes were coated with VEGF (SEQ ID NO: 5), a high-affinity ligand for VEGF receptors, which are expressed at high levels by human umbilical vein endothelial cells (HUVECs). HUVECs were incubated with silica-coated FITC-conjugated polyplexes with poly(L-arginine) (SEQ ID NO: 4) or human VEGF (SEQ ID NO: 5) attached to the outer surface of the silica coating for 40 min before being washed twice with PBS then resuspended in DMEM (10% FBS). Cells were imaged 4 hrs later. After this short incubation period, only low levels of transfection with nanoparticles containing a poly(L-arginine) layer attached to the external silica surface (FIG. 9A) was observed, whereas coating with VEGF instead of poly(L-arginine) resulted in significantly greater cellular internalization at this four-hour time point. A skilled artisan would recognize that virtually any other cell type may also be transfected by nanoparticles in accordance with the present invention, and that a layer of polymers may be attached to the outer layer of silica-coated polyplex cores to promote or otherwise influence this effect. Such a person would also comprehend that other means of contacting cells with nanoparticles to effect such outcomes, such as i.p., i.v., i.m. or s.c. or other injection or transdermal administration or via suppository to, or ingestion or oral or nasal inhalation by, a human or animal, or contact with explanted tissue or cells or stem cells, would also be included within the present invention.

In another aspect of the invention, a polynucleotide encoding a nuclease may be incorporated into the nanoparticle polyplex core. As one nonlimiting example, a polynucleotide that encodes and drives expression of a TALEN (Transcription Factor-Like Effector Nucleases) may be included in the nanoparticle. Like Zinc Finger Nucleases, TALENs utilize a modular DNA binding motif (TALE) that can be modified to introduce new DNA binding specificities and even nucleases (TALEN). TALEs consist of multiple repeat variable diresidues (RVDs) which each specify binding to a single nucleotide. TALE arrays are made by stringing together RVDs in a specific order to provide specificity and binding affinity to desired DNA sequences. Commonly, these genome-splicing tools are engineered by fusing non-specific cleavage domains, such as FokI nucleases, to TALEs. TALEN assembly protocols are available that allow assembly of these repetitive sequences, including an open source assembly method known as Golden Gate.

In another aspect of the present invention, nanoparticles may be designed and used in a manner to regulate expression of signaling molecules to alter cellular function. For example, sequences of chromosomal DNA may be deleted or altered to generate cellular or animal models of disease states or treatments therefor, or to treat disease states or otherwise enhance human health. One nonlimiting example of a protein whose expression may be modified in accordance with the present invention is sclerostin (SOST). SOST binding to the LRP5/6 receptor inhibits Wnt signaling, perhaps via feedback systems between Wnt3A, Wnt7B, Wnt1 OA, sclerostin, β-catenin, LEF1, and TCF1. Desuppressing these cascades via removal of sclerostin may result in significantly increased mineralization activity.

Osteoprogenitor (OPG) and RANKL are also expected to play a responsive role to SOST deletion, where RANKL expresses itself as a receptor for promoting osteoclastogenesis via osteoclast-linked RANK or ODF (osteoclast differentiation factor) binding, and OPG binds antagonistically to RANKL. Thus, the ratio between OPG and RANKL is a determinant of the relationship between bone formation and resorption. However, single cultures of osteoblasts will communicate through other forms of paracrine signaling and this ratio should be more reflective of behavior of altered cells in co-culture with osteoclasts or in vivo.

Figure 10:
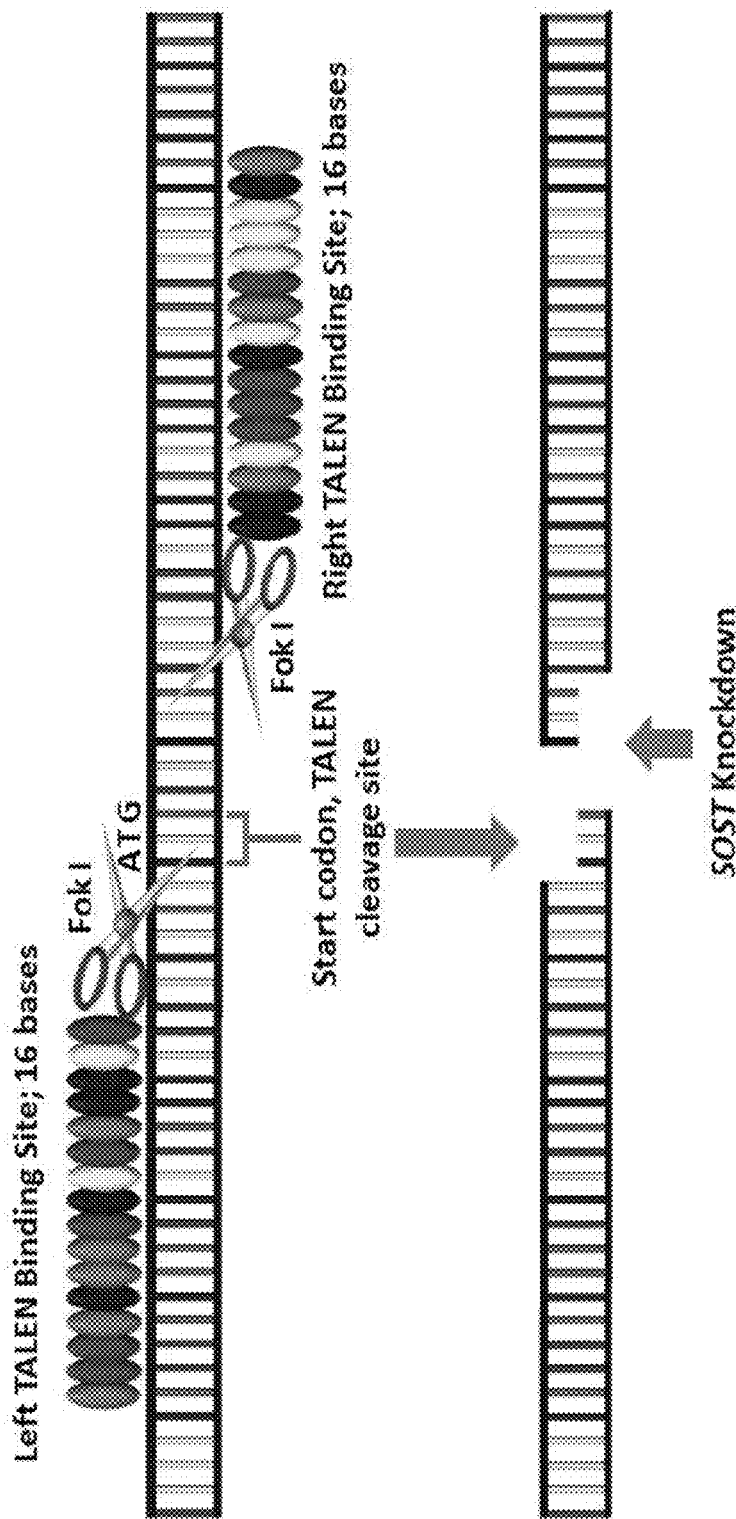
FIG. 10 is a diagrammatic representation of TALEN peptides encoded for by a nucleic acid included in a nanoparticle that cause knockdown of expression of sclerostin in accordance with an aspect of the present invention.

In another aspect of the present invention, a nanoparticle may be designed so as to allow transfection with a TALEN that may disrupt expression of SOST and consequently generate a high bone-mass phenotype. As one example, TALENS may be engineered to specifically bind to loci in the SOST gene and create double-stranded breaks in the genome to disrupt transcription or translation and reduce SOST expression. As a further example, a nanoparticle may contain plasmids that encode two TALENs that create double-stranded breaks on either side of the chromosomal locus of the start codon for SOST. Repair of endogenous genomic DNA following excision of the sequence encoding the start codon may result in transcription of sclerostin mRNA lacking the start codon that cannot be properly translated into SOST protein, thereby driving down SOST expression and activity. A diagrammatic representation of this model is shown in FIG. 10, where a "left" TALEN and "right" TALEN bind and cleave sites on opposite sides of the SOST start codon locus. As one example, a left TALEN may have the sequence represented by SEQ ID NO: 6, and a right TALEN may have the sequence represented by SEQ ID NO: 7. A nanoparticle may comprise an expression plasmid, such as pUC19 (Genbank Accession Number L09137 X02514), into which a nucleotide sequence that encodes a right or left TALEN, such as those represented by SEQ ID NO: 6 and SEQ ID NO: 7, has been subcloned so as to drive cellular expression of the encoded TALEN. A nanoparticle may also include combinations of expression plasmids that comprise sequences that encode left and right TALENs.

A nanoparticle may also comprise other TALEN sequences, targeting SOST or any other gene of interest, and also may comprise other expression vectors, in accordance with the present invention. A nanoparticle may comprise other types of polynucleotides or analogs thereof, such as species of RNA or DNA including mRNA, siRNA, miRNA, aptamers, shRNA, AAV-derived nucleic acids, morpholeno RNA, peptoid and peptide nucleic acids, cDNA, DNA origami, DNA and RNA with synthetic nucleotides, DNA and RNA with predefined secondary structures, CRISPR sequences, and multimers and oligomers, and any combination of the foregoing, in accordance with the present invention. In another example, a nanoparticle may comprise polynucleotides whose sequence may encode other products such as any protein or polypeptide whose expression is desired. A skilled artisan would recognize that the foregoing examples are in accordance with the present invention and may be encompassed by claims thereto.

Figure 11A:
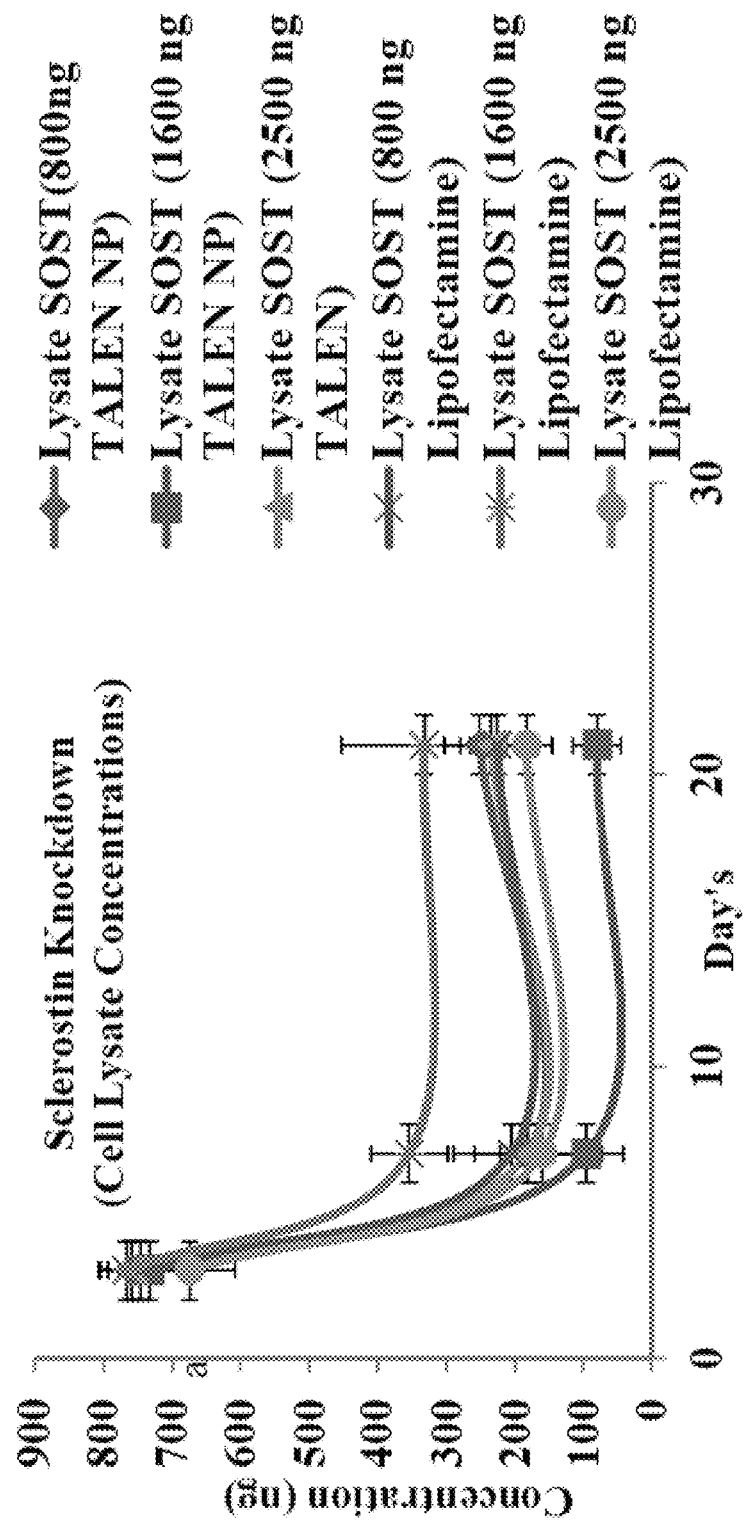
FIGS. 11A-11C are graphs illustrating the effects transfecting cells with different amounts of nanoparticles that target sclerostin expression on sclerostin and β-catenin expression in accordance with an aspect of the present invention.
Figure 11B:
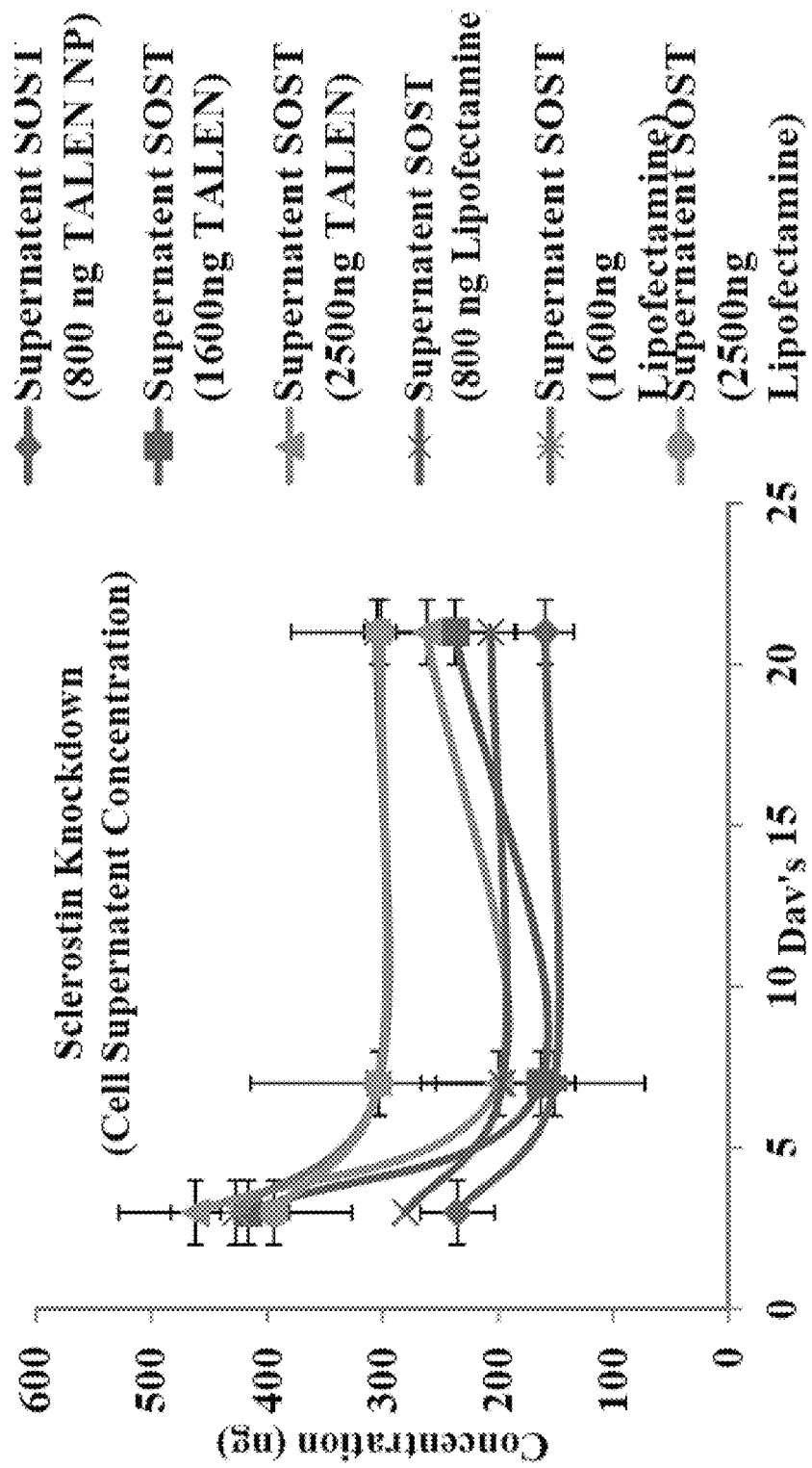
Figure 11C:
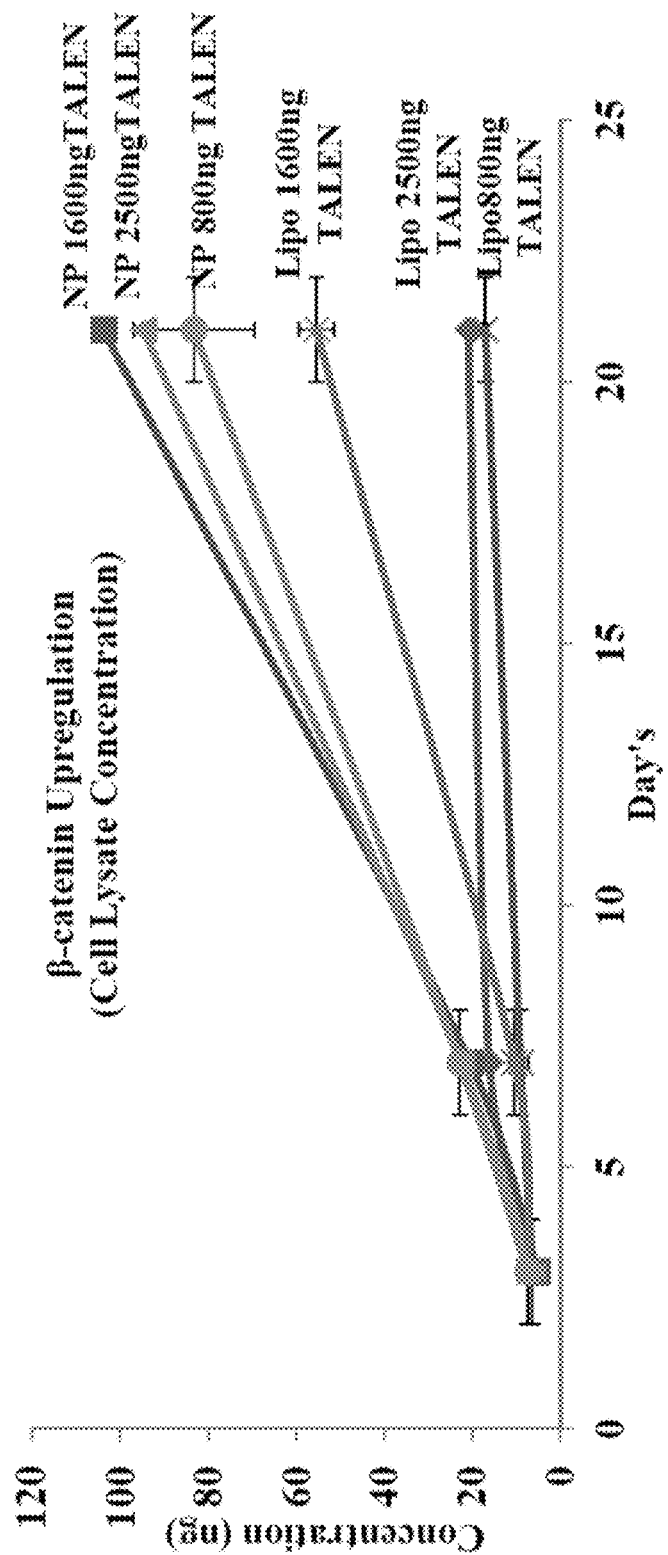
Figure 12A:
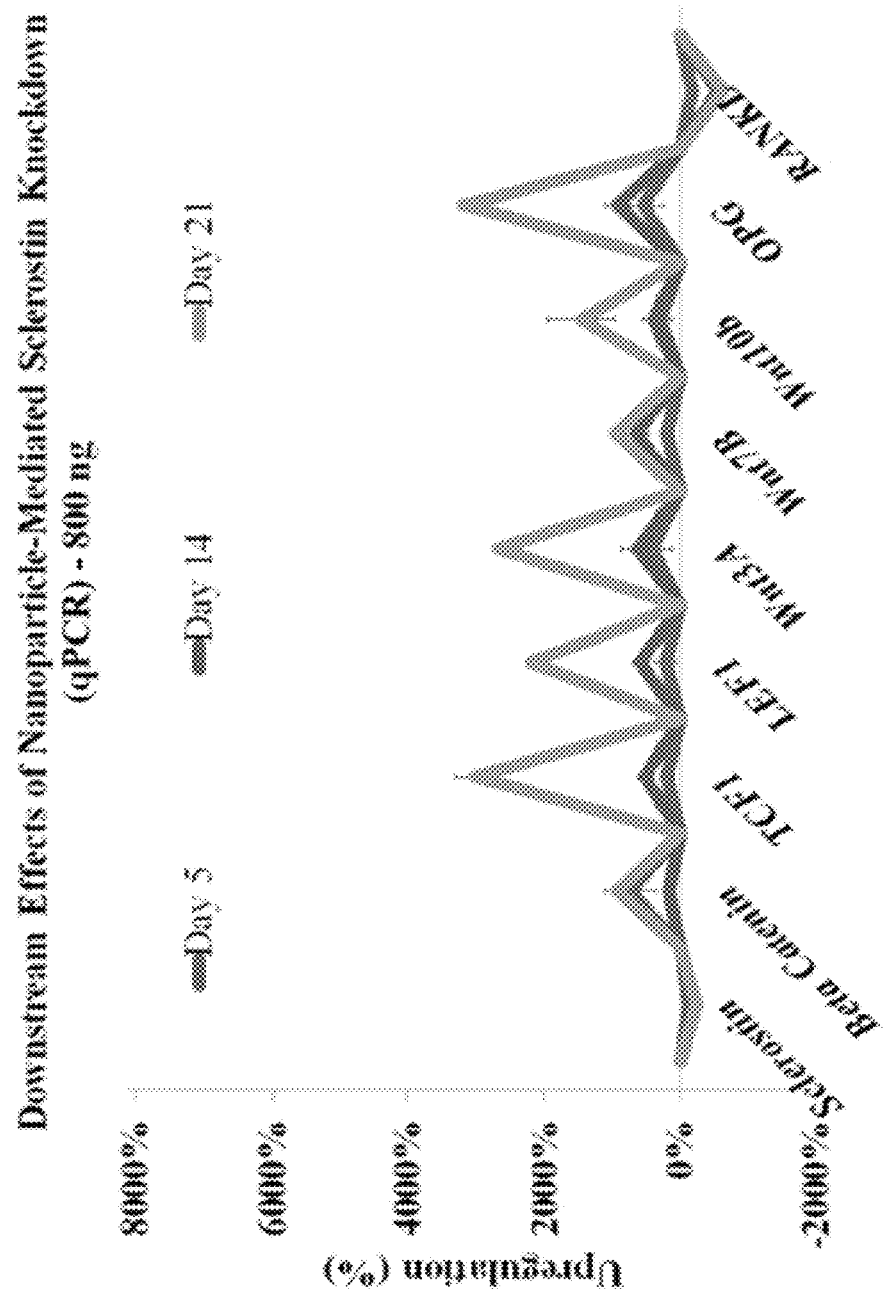
FIGS. 12A-12F are graphs illustrating the effects of transfecting cells with different amounts of nanoparticles that target sclerostin expression on expression levels of various cellular signaling peptides in accordance with an aspect of the present invention.
Figure 12B:
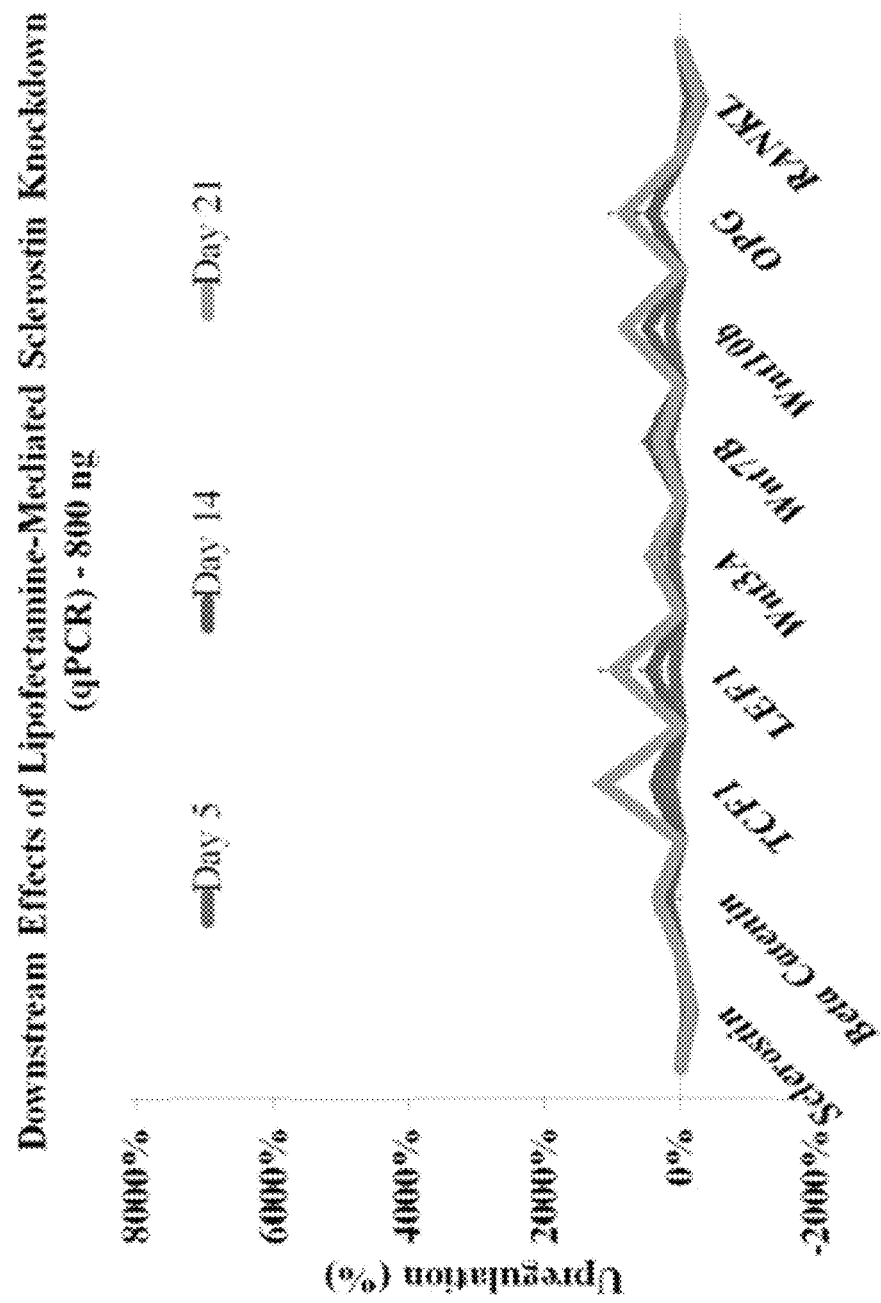
Figure 12C:
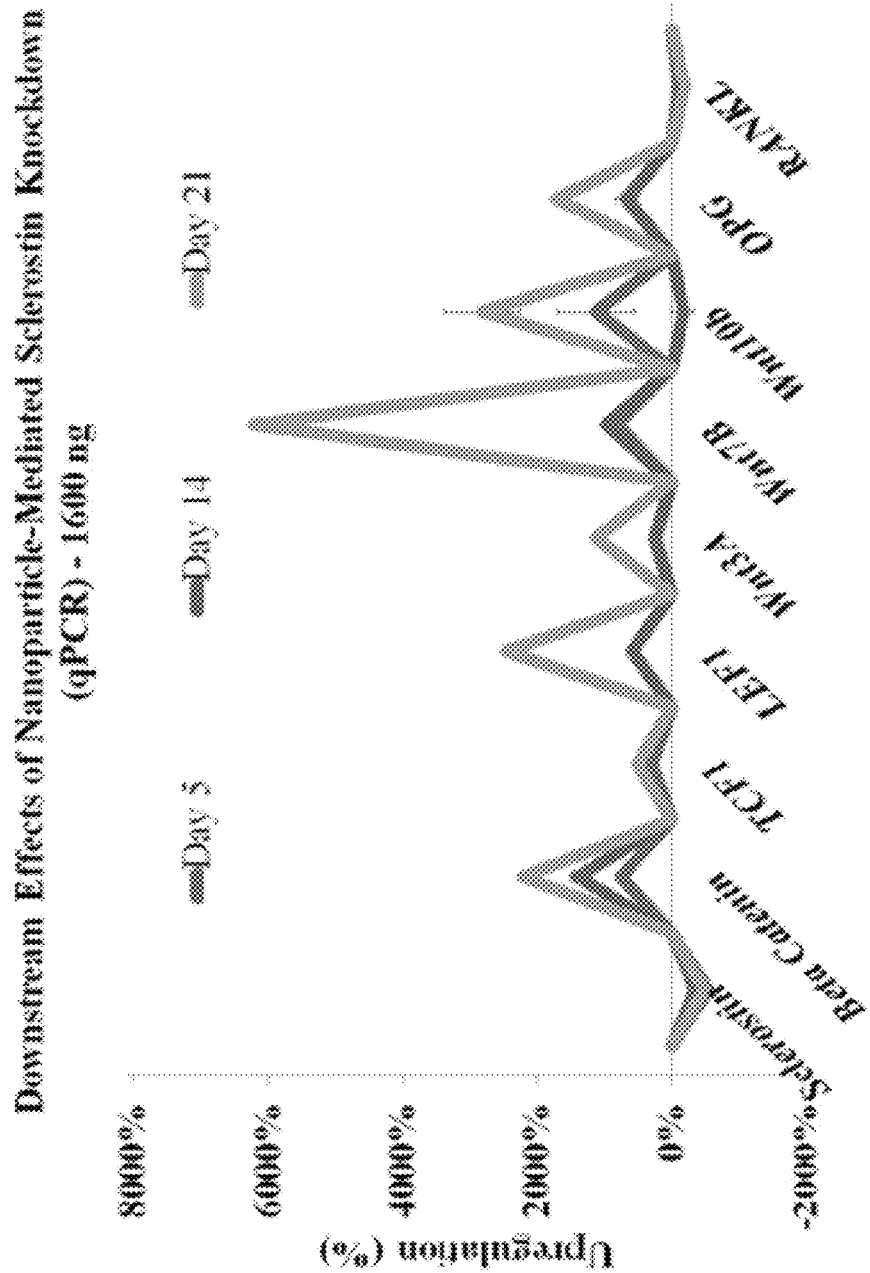
Figure 12D:
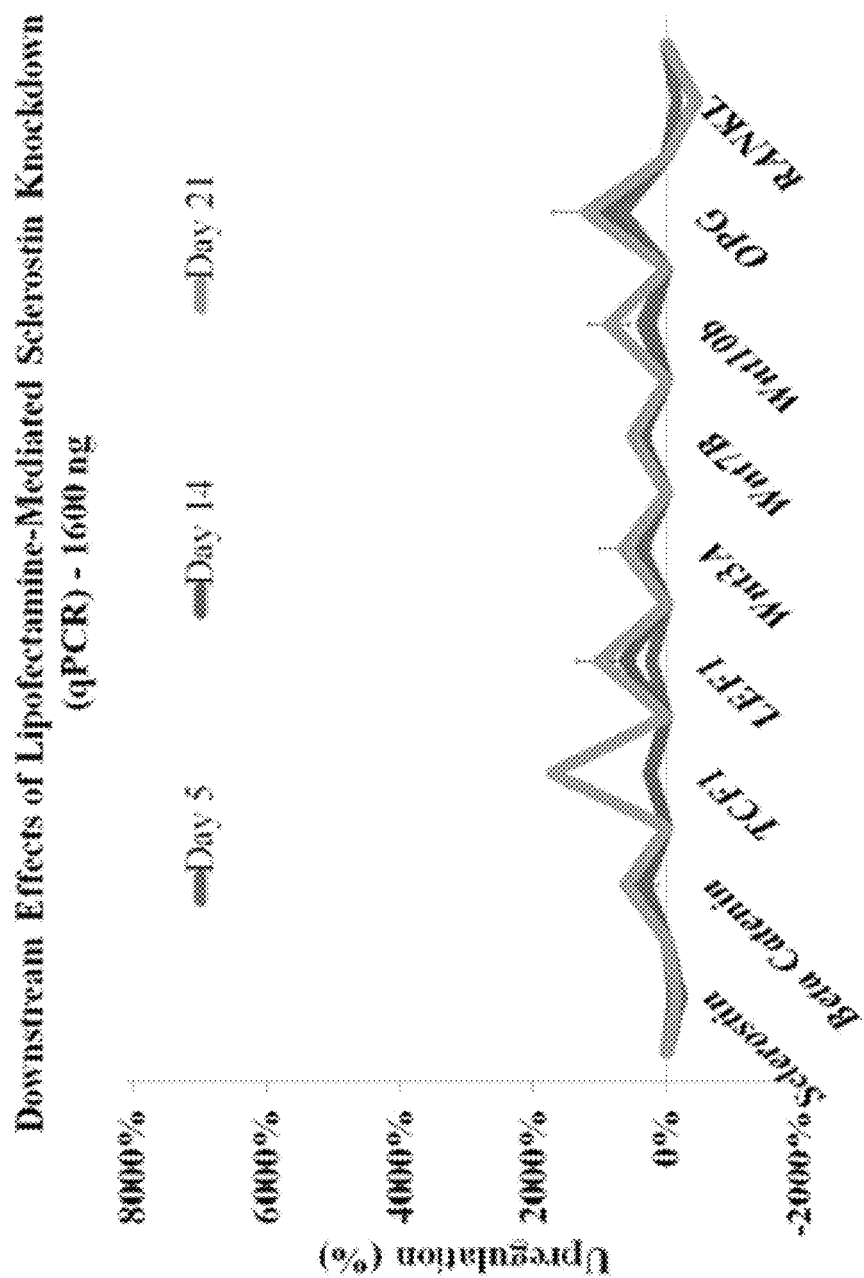
Figure 12E:
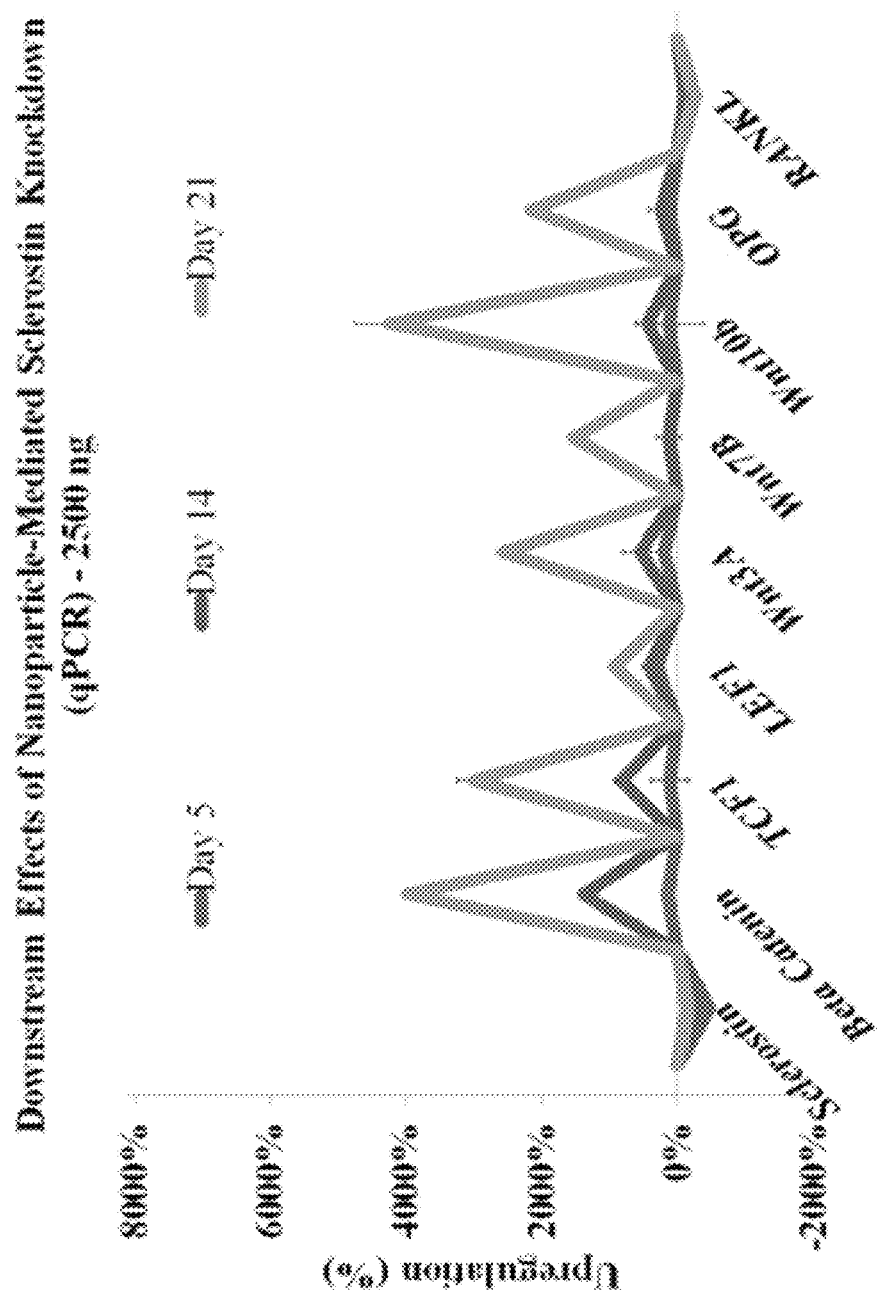
Figure 12F:
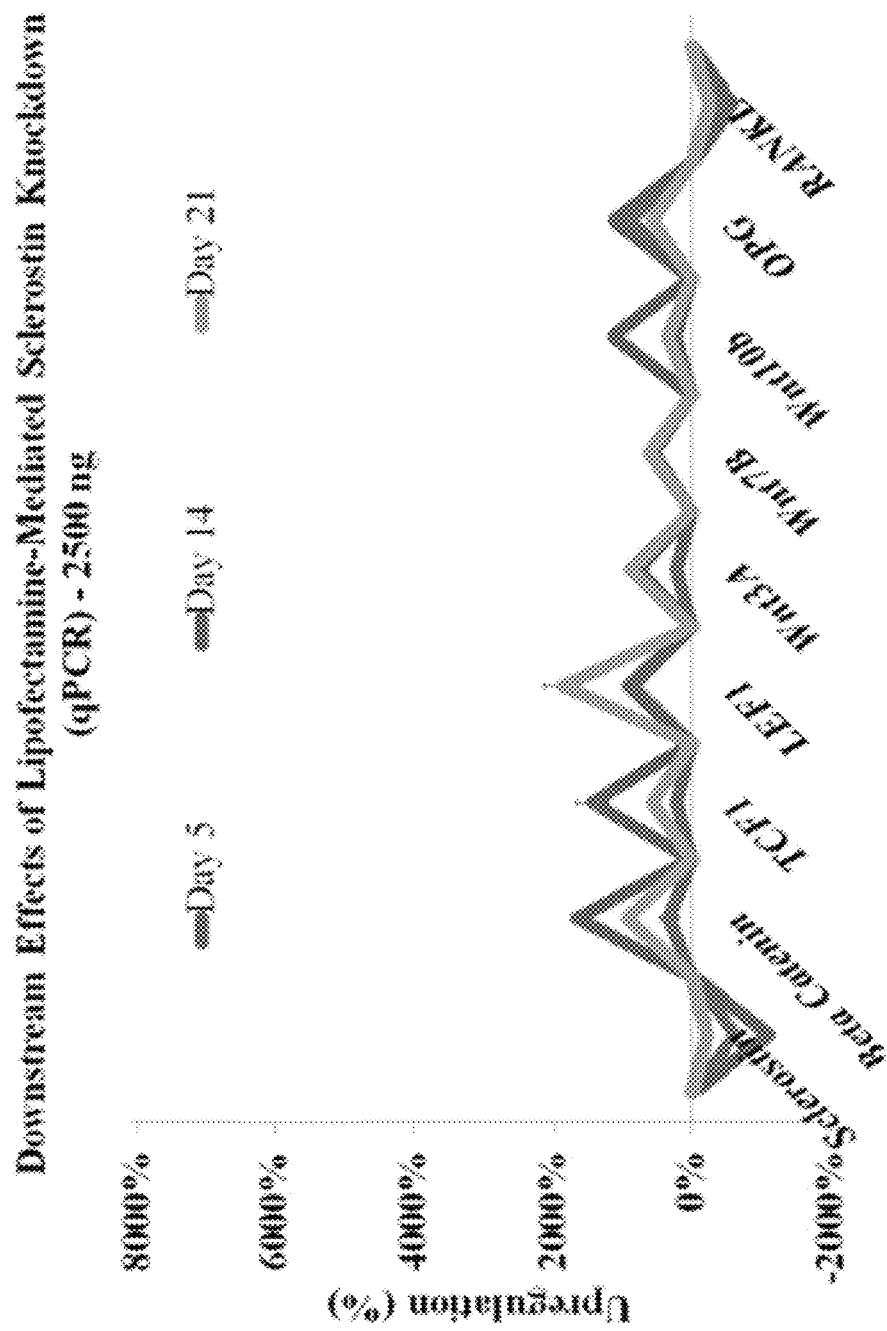

Following transfection of MC3T3 murine osteoblasts with nanoparticles designed to knock down SOST expression in accordance with the present invention, ELISA and quantitative real-time PCR (qPCR) assays were performed on cell lysate and supernatant fractions. FIGS. 11A-11C are graphs demonstrating the effectiveness of different amounts (800 ng, 1600 ng, or 2500 ng) of nanoparticles (NP) containing expression plasmids comprising nucleotide sequences that encode left (SEQ ID NO: 6) and right (SEQ ID NO: 7) SOST TALENs, in accordance with the present invention, in modulating SOST expression and β-catenin expression over a period of up to over 20 days following transfection. For comparison, other cells were transfected with mRNA encoding the same TALENS using Lipofectamine, a known agent for cellular transfection. As shown in FIGS. 11A-11C, intracellular and extracellular SOST levels were suppressed for at least several weeks following transfection with nanoparticles in accordance with the present invention, whereas β-catenin expression was concomitantly up-regulated, signifying effectiveness of the nanoparticles in downregulating SOST expression and activity.

qPCR was also performed to determine whether downregulation of SOST expression with nanoparticles in accordance with the present invention may have downstream effects on other components of the relevant signaling cascade. Cells were transfected as described above. Results on expression of numerous components of the signaling pathway (SOST, β-catenin, TCF1, LEF1, Wnt3A, Wnt7B, Wnt10b, OPG, and RANKL), at 5, 14, and 21 days after transfection with different amounts of nanoparticles as indicated, are shown in FIGS. 12A-12F. For comparison, other cells were transfected with mRNA encoding the same TALENS using Lipofectamine. The real time PCR results showed a greater up regulation of Wnt responsive genes in the cell lines transfected with nanoparticles delivering SOST TALENS as compared to the SOST TALENS delivered by Lipofectamine by up to 2 to 6 times as a response to knockdown of the Wnt signaling inhibitor sclerostin.

Figure 13:
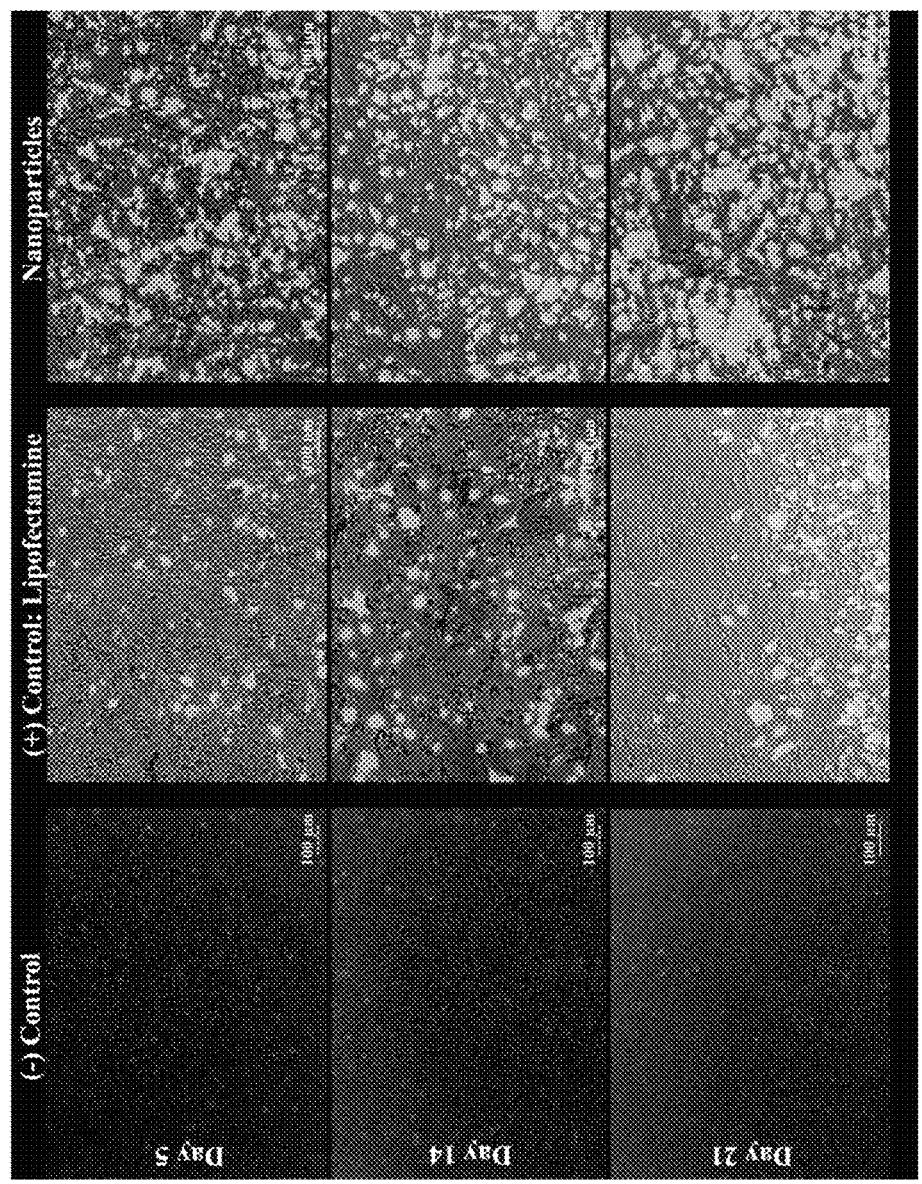
FIG. 13 is photomicrographs demonstrating effects of transfecting cells with nanoparticles that target sclerostin expression on expression of a co-transfected reporter gene that is responsive to transcription factors whose activity is inhibited by sclerostin-mediated signaling in accordance with an aspect of the present invention.

TCF/LEF-1-mediated transcription may also be upregulated following knockdown of SOST expression in accordance with the present invention. MC3T3-E1 cells were transfected with TOPflash and control FOPflash luciferase reporter plasmid constructs (Addgene#12456 and 12457) that contain TCF/LEF-1 binding sites. The cells were plated at the density of 5000 cells/well of the 8-well labtek chamber slides and transfected with 1 ug of TOPflash and FOPflash plasmid separately. To control for the efficiency of transfection a control plasmid Renilla (Promega) was used. FIG. 13 is photomicrographs showing upregulation of TCF/LEF-1-mediated transcription for 21 days following tranfection with nanoparticles containing plasmids encoding SOST-directed TALENS, in accordance with the present invention, consistent with an upregulation of TCF/LEF-1 expression and activity following transfection with the invented nanoparticles.

Knockdown of SOST expression in accordance with the present invention may also increase mineralization in stromal bone marrow cells and osteoblasts. Mineralization was quantified by two separate methods, first based on image thresholding of xylenol-orange-labeled vital cultures using MATLAB (Mathworks, Natick, MA), and second by atomic absorption spectroscopy (AAS). For the xylenol orange threshold, images of both phase and fluorescence (with Texas Red Filter Set) were taken in five adjacent regions of wells, and then stitched into a larger 8-bit image (4x, Nikon Ti-100). The phase channel was subtracted from the fluorescence, and a threshold was set to half the level between the background and signal (−6 dB). The number of pixels above the threshold were counted and used to express the percentage of mineralized area in each well. The combination of phase and fluorescence allowed for unbound xylenol orange to be distinguished, whereas the use of decibel levels allowed for correction of the varied background levels in each image.

Mineralization was also quantified by atomic absorption with an atomic absorption spectrometer (AA-Perkin Elmer, MA). Each well was prepared by adding 0.5 mL of 10% nitric acid, and the resultant calcium content was measured relative to a standard curve and compared between groups. Care was taken to minimize interference due to ionized calcium precipitating with phosphate phases, so a large excess of potassium and lanthanum ions was added to each well.

Figure 14A:
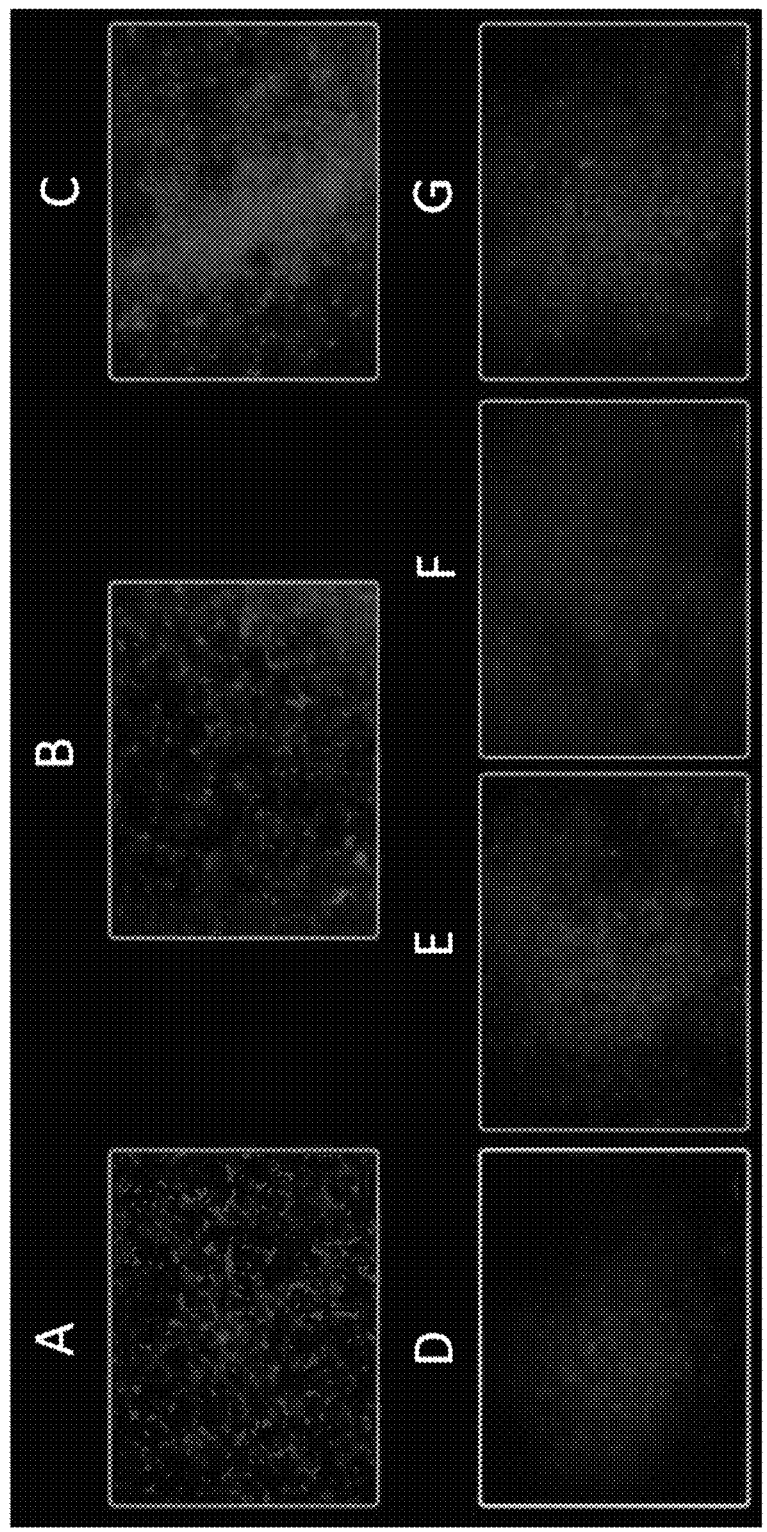
FIGS. 14A-14C are photomicrographs demonstrating effects of transfecting cells with nanoparticles that target sclerostin expression on mineralization in accordance with an aspect of the present invention.
Figure 14B:
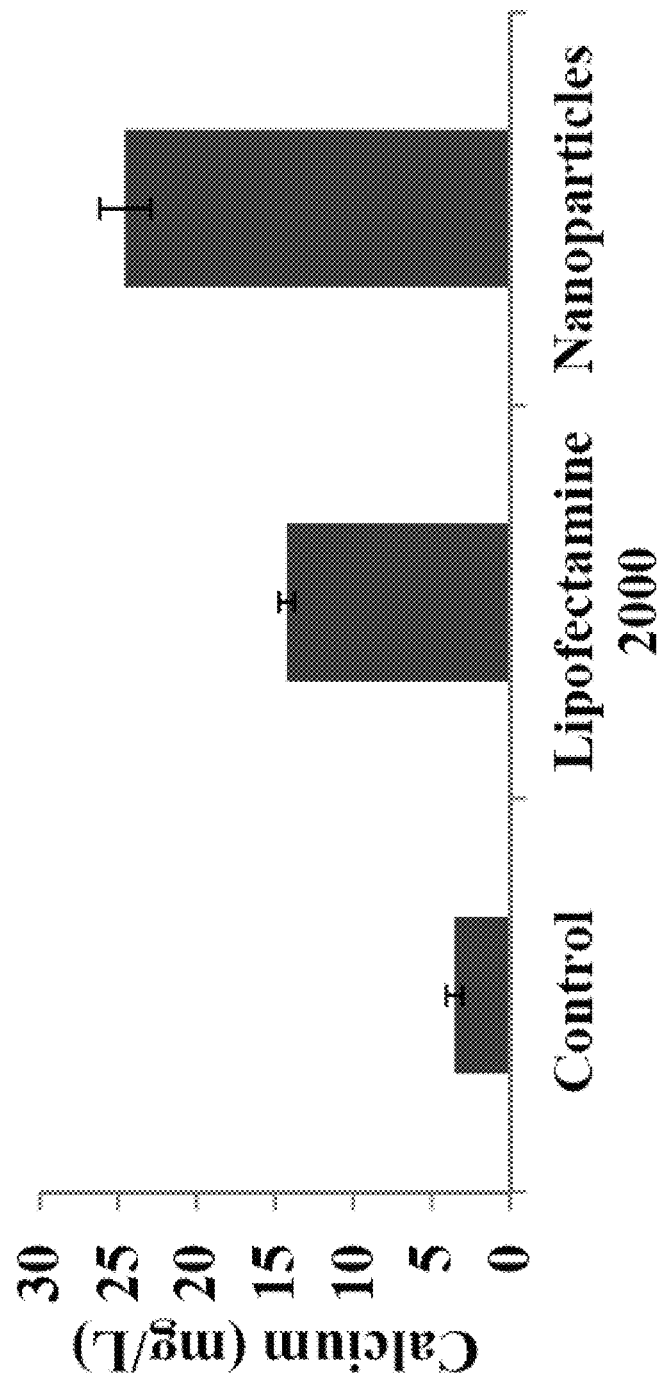
Figure 14C:
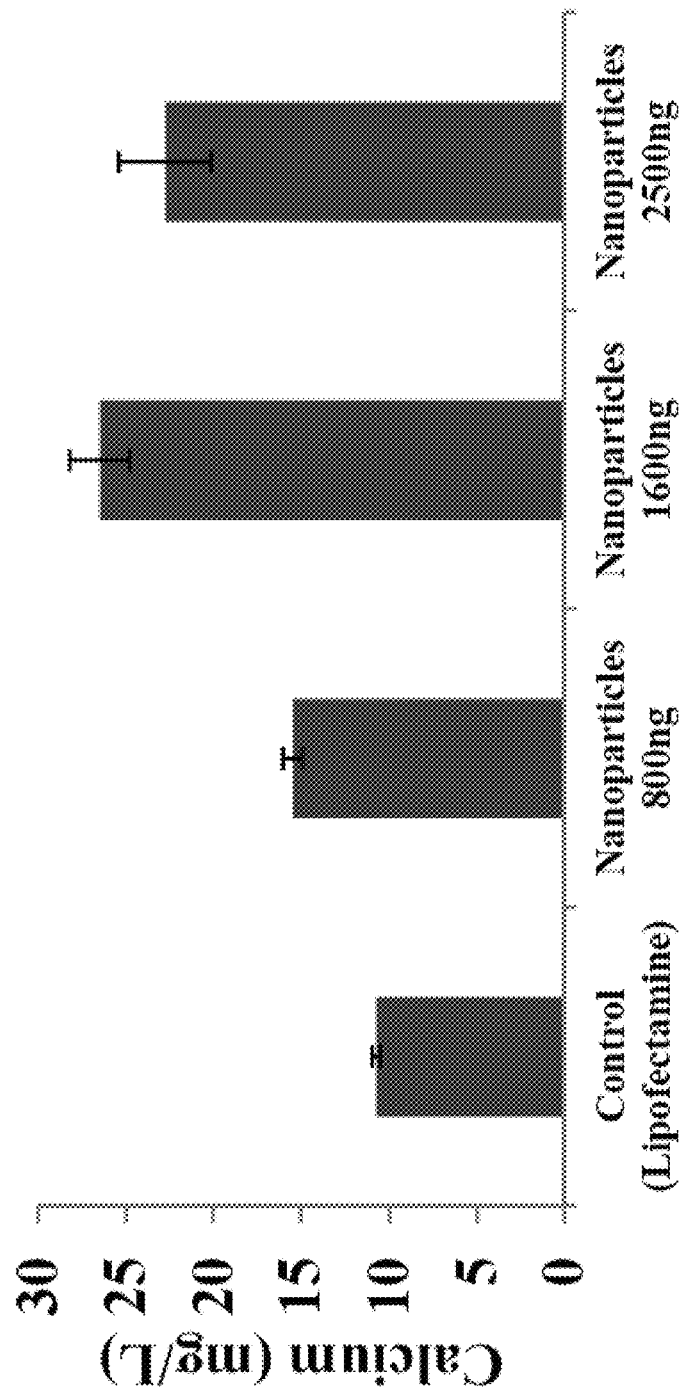

FIGS. 14A-14C show the effects of transfection with nanoparticles in accordance with the present invention on mineralization following SOST knockdown. FIG. 14A is photomicrographs of staining of the mineralized matrix formed 25 days after SOST knockdown. Stromal cells are shown in panels A-C, wherein panel A show control cells, panel B shows cells transfected via Lipofectamine, and panel C shows cells transfected with nanoparticles containing plasmids encoding SOST-directed TALENs as described and in accordance with the present invention. MC3T3-E1 osteoblast cells are shown in panels D-G, wherein panel D show control cells, and panels E-G show cells transfected with nanoparticles containing plasmids encoding SOST-directed TALENs as described at doses of 800 ng, 1600 ng, and 2500 ng, respectively, in accordance with the present invention. FIGS. 14B and 14C are graphs showing quantification of mineralization. FIGS. 14A-C demonstrate increased calcium concentration in stromal bone marrow cells and osteoblasts following transfection with SOST-targetting TALENS via nanoparticles in accordance with the present invention, further confirming the effectiveness of this technique of modifying the cellular expression and activity of genes and downstream signaling pathways.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

The invention claimed is:

1. A nanoparticle comprising:
   a core polyplex comprising a cationic polymer, a cationic polypeptide, a polynucleotide, and one or more anionic polymers, wherein the one or more anionic polymers is selected from the group consisting of poly(D-glutamic acid), a glycosaminoglycan, a glycoprotein, a polysaccharide, poly(mannuronic acid), poly(guluronic acid), heparin, heparin sulfate, chondroitin, chondroitin sulfate, keratan, keratan sulfate, aggrecan, poly(glucosamine), and any combination of two or more of the foregoing;
   a silica coating on the core polyplex; and
   poly(L-arginine), a vasoactive endothelial growth factor peptide, or both attached to an outer surface of said silica coating; wherein
   the cationic polymer and the one or more anionic polymers are not covalently bound to each other.

2. The nanoparticle of claim 1 wherein the anionic polymer is poly(D-glutamic acid).

3. The nanoparticle of claim 1 wherein the cationic polymer is selected from the group consisting of poly(ethylenimine) and poly(L-arginine).

4. The nanoparticle of claim 1 wherein the cationic polypeptide is a histone tail peptide.

5. The nanoparticle of claim 4 wherein the histone tail peptide is human H3 histone tail peptide.

6. The nanoparticle of claim 1 wherein the anionic polymer is poly(D-glutamic acid), the cationic polymer is selected from the group consisting of poly(ethylenimine) and poly(L-arginine), and the cationic polypeptide is a histone tail peptide.

7. The nanoparticle of claim 6 wherein the polynucleotide comprises a nucleotide sequence that encodes a nuclease.

8. The nanoparticle of claim 7 wherein the nuclease is a TALEN.

9. The nanoparticle of claim 8 wherein the TALEN is capable of inducing a break at a site-specific locus of DNA, wherein the break results in a change of expression of a protein encoded by a gene.

10. The nanoparticle of claim 9 wherein the change is a decrease and the gene encodes a sclerostin protein.

11. A nanoparticle comprising:
    a core polyplex comprising a cationic polymer, a cationic polypeptide, a polynucleotide, and one or more anionic polymers, wherein the one or more anionic polymers is selected from the group consisting of poly(D-glutamic acid), a glycosaminoglycan, a glycoprotein, a polysaccharide, poly(mannuronic acid), poly(guluronic acid), heparin, heparin sulfate, chondroitin, chondroitin sulfate, keratan, keratan sulfate, aggrecan, poly(glucosamine), and any combination of two or more of the foregoing; and
    a silica coating on the core polyplex; wherein
    the cationic polymer and the one or more anionic polymers are not covalently bound to each other.

12. The nanoparticle of claim 11 wherein the anionic polymer is poly(D-glutamic acid).

13. The nanoparticle of claim 11 wherein the cationic polymer is selected from the group consisting of poly(ethylenimine) and poly(L-arginine).

14. The nanoparticle of claim 11 wherein the cationic polypeptide is a histone tail peptide.

15. The nanoparticle of claim 14 wherein the histone tail peptide is human H3 histone tail peptide.

16. The nanoparticle of claim 11 wherein the anionic polymer is poly(D-glutamic acid), the cationic polymer is selected from the group consisting of poly(ethylenimine) and poly(L-arginine), and the cationic polypeptide is a histone tail peptide.

17. The nanoparticle of claim 16 wherein the polynucleotide comprises a nucleotide sequence that encodes a nuclease.

18. The nanoparticle of claim 17 wherein the nuclease is a TALEN.

19. The nanoparticle of claim 18 wherein the TALEN is capable of inducing a break at a site-specific locus of DNA, wherein the break results in a change of expression of a protein encoded by a gene.

20. The nanoparticle of claim 19 wherein the change is a decrease and the gene encodes a sclerostin protein.

21. A nanoparticle of claim 16, further comprising a polymer attached to an outer surface of said silica coating.

22. A nanoparticle of claim 21, wherein said polymer attached to an outer surface of said silica coating comprises one or more of poly(L-arginine) or a vasoactive endothelial growth factor peptide.

23. A nanoparticle comprising:
a core polyplex comprising poly(D-glutamic acid), a cationic polymer comprising poly(ethylenimine) or poly(L-arginine), or both, a polynucleotide, and a histone tail peptide,
a silica coating on the core polyplex, and
poly(L-arginine), a vasoactive endothelial growth factor peptide, or both attached to an outer surface of said silica coating; wherein
the poly(D-glutamic acid) and the cationic polymer are not covalently bound to each other.

* * * * *

SEQUENCE LISTING

```
<160> NUMBER OF SEQ ID NOS: 13

<210> SEQ ID NO 1
<211> LENGTH: 186
<212> TYPE: PRT
<213> ORGANISM: Artificial Sequence
<220> FEATURE:
<223> OTHER INFORMATION: Laboratory-synthesized sequence.

<400> SEQUENCE: 1

Arg Arg Arg Arg Arg Arg Arg Arg Arg Arg Arg Arg Arg Arg Arg Arg
1               5                   10                  15

Arg Arg Arg Arg Arg Arg Arg Arg Arg Arg Arg Arg Arg Arg Arg Arg
            20                  25                  30

Arg Arg Arg Arg Arg Arg Arg Arg Arg Arg Arg Arg Arg Arg Arg Arg
        35                  40                  45

Arg Arg Arg Arg Arg Arg Arg Arg Arg Arg Arg Arg Arg Arg Arg Arg
    50                  55                  60

Arg Arg Arg Arg Arg Arg Arg Arg Arg Arg Arg Arg Arg Arg Arg Arg
65                  70                  75                  80

Arg Arg Arg Arg Arg Arg Arg Arg Arg Arg Arg Arg Arg Arg Arg Arg
                85                  90                  95

Arg Arg Arg Arg Arg Arg Arg Arg Arg Arg Arg Arg Arg Arg Arg Arg
            100                 105                 110
```

Arg Arg Arg Arg Arg Arg Arg Arg Arg Arg Arg Arg
            115                 120                 125

Arg Arg Arg Arg Arg Arg Arg Arg Arg Arg Arg Arg
        130                 135                 140

Arg Arg Arg Arg Arg Arg Arg Arg Arg Arg Arg Arg
145                 150                 155                 160

Arg Arg Arg Arg Arg Arg Arg Arg Arg Arg Arg Arg
            165                 170                 175

Arg Arg Arg Arg Arg Arg Arg Arg
        180                 185

<210> SEQ ID NO 2
<211> LENGTH: 116
<212> TYPE: PRT
<213> ORGANISM: Artificial Sequence
<220> FEATURE:
<223> OTHER INFORMATION: Laboratory-created sequence.
<220> FEATURE:
<221> NAME/KEY: MISC_FEATURE
<222> LOCATION: (1)..(116)
<223> OTHER INFORMATION: D isomer.

<400> SEQUENCE: 2

Glu Glu Glu Glu Glu Glu Glu Glu Glu Glu Glu Glu Glu Glu Glu Glu
1               5                   10                  15

Glu Glu Glu Glu Glu Glu Glu Glu Glu Glu Glu Glu Glu Glu
            20                  25                  30

Glu Glu Glu Glu Glu Glu Glu Glu Glu Glu Glu Glu Glu Glu
        35                  40                  45

Glu Glu Glu Glu Glu Glu Glu Glu Glu Glu Glu Glu Glu Glu
    50                  55                  60

Glu Glu Glu Glu Glu Glu Glu Glu Glu Glu Glu Glu Glu Glu Glu Glu
65                  70                  75                  80

Glu Glu Glu Glu Glu Glu Glu Glu Glu Glu Glu Glu Glu Glu
            85                  90                  95

Glu Glu Glu Glu Glu Glu Glu Glu Glu Glu Glu Glu Glu Glu
        100                 105                 110

Glu Glu Glu Glu
        115

<210> SEQ ID NO 3
<211> LENGTH: 25
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: TRIMETHYLATION.
<220> FEATURE:
<221> NAME/KEY: MISC_FEATURE
<222> LOCATION: (25)..(25)
<223> OTHER INFORMATION: AMIDATED.

<400> SEQUENCE: 3

Ala Arg Thr Lys Gln Thr Ala Arg Lys Ser Thr Gly Gly Lys Ala Pro
1               5                   10                  15

Arg Lys Gln Leu Ala Thr Lys Ala Ala
            20                  25

<210> SEQ ID NO 4
<211> LENGTH: 64
<212> TYPE: PRT

```
<213> ORGANISM: Artificial Sequence
<220> FEATURE:
<223> OTHER INFORMATION: Laboratory-created sequence.

<400> SEQUENCE: 4

Arg Arg Arg Arg Arg Arg Arg Arg Arg Arg Arg Arg Arg Arg Arg
1               5                   10                  15

Arg Arg Arg Arg Arg Arg Arg Arg Arg Arg Arg Arg Arg Arg Arg
                20                  25                  30

Arg Arg Arg Arg Arg Arg Arg Arg Arg Arg Arg Arg Arg Arg Arg
            35                  40                  45

Arg Arg Arg Arg Arg Arg Arg Arg Arg Arg Arg Arg Arg Arg Arg
        50                  55                  60

<210> SEQ ID NO 5
<211> LENGTH: 165
<212> TYPE: PRT
<213> ORGANISM: Homo sapiens

<400> SEQUENCE: 5

Ala Pro Met Ala Glu Gly Gly Gln Asn His His Glu Val Val Lys
1               5                   10                  15

Phe Met Asp Val Tyr Gln Arg Ser Tyr Cys His Pro Ile Glu Thr Leu
                20                  25                  30

Val Asp Ile Phe Gln Glu Tyr Pro Asp Glu Ile Glu Tyr Ile Phe Lys
            35                  40                  45

Pro Ser Cys Val Pro Leu Met Arg Cys Gly Gly Cys Cys Asn Asp Glu
        50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160

Asp Lys Pro Arg Arg
                165

<210> SEQ ID NO 6
<211> LENGTH: 936
<212> TYPE: PRT
<213> ORGANISM: Artificial Sequence
<220> FEATURE:
<223> OTHER INFORMATION: Laboratory-created sequence.

<400> SEQUENCE: 6

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
                20                  25                  30

Ser Gln Gln Gln Gln Glu Lys Ile Lys Pro Lys Val Arg Ser Thr Val
            35                  40                  45

Ala Gln His His Glu Ala Leu Val Gly His Gly Phe Thr His Ala His
```

```
            50              55              60
Ile Val Ala Leu Ser Gln His Pro Ala Leu Gly Thr Val Ala Val
 65                  70                  75                  80
Lys Tyr Gln Asp Met Ile Ala Ala Leu Pro Glu Ala Thr His Glu Ala
                     85                  90                  95
Ile Val Gly Val Gly Lys Gln Trp Ser Gly Ala Arg Ala Leu Glu Ala
                100                 105                 110
Leu Leu Thr Val Ala Gly Glu Leu Arg Gly Pro Pro Leu Gln Leu Asp
                115                 120                 125
Thr Gly Gln Leu Leu Lys Ile Ala Lys Arg Gly Gly Val Thr Ala Val
            130                 135                 140
Glu Ala Val His Ala Trp Arg Asn Ala Leu Thr Gly Ala Pro Leu Asn
145                 150                 155                 160
Leu Thr Pro Gln Gln Val Val Ala Ile Ala Ser Asn Asn Gly Gly Lys
                165                 170                 175
Gln Ala Leu Glu Thr Val Gln Arg Leu Leu Pro Val Leu Cys Gln Ala
                180                 185                 190
His Gly Leu Thr Pro Glu Gln Val Val Ala Ile Ala Ser His Asp Gly
                195                 200                 205
Gly Lys Gln Ala Leu Glu Thr Val Gln Arg Leu Leu Pro Val Leu Cys
            210                 215                 220
Gln Ala His Gly Leu Thr Pro Glu Gln Val Val Ala Ile Ala Ser His
225                 230                 235                 240
Asp Gly Gly Lys Gln Ala Leu Glu Thr Val Gln Arg Leu Leu Pro Val
                245                 250                 255
Leu Cys Gln Ala His Gly Leu Thr Pro Glu Gln Val Val Ala Ile Ala
                260                 265                 270
Ser His Asp Gly Gly Lys Gln Ala Leu Glu Thr Val Gln Arg Leu Leu
            275                 280                 285
Pro Val Leu Cys Gln Ala His Gly Leu Thr Pro Gln Gln Val Val Ala
            290                 295                 300
Ile Ala Ser Asn Gly Gly Gly Lys Gln Ala Leu Glu Thr Val Gln Arg
305                 310                 315                 320
Leu Leu Pro Val Leu Cys Gln Ala His Gly Leu Thr Pro Glu Gln Val
                325                 330                 335
Val Ala Ile Ala Ser His Asp Gly Gly Lys Gln Ala Leu Glu Thr Val
                340                 345                 350
Gln Arg Leu Leu Pro Val Leu Cys Gln Ala His Gly Leu Thr Pro Glu
            355                 360                 365
Gln Val Val Ala Ile Ala Ser His Asp Gly Gly Lys Gln Ala Leu Glu
            370                 375                 380
Thr Val Gln Arg Leu Leu Pro Val Leu Cys Gln Ala His Gly Leu Thr
385                 390                 395                 400
Pro Gln Gln Val Val Ala Ile Ala Ser Asn Gly Gly Gly Lys Gln Ala
                405                 410                 415
Leu Glu Thr Val Gln Arg Leu Leu Pro Val Leu Cys Gln Ala His Gly
                420                 425                 430
Leu Thr Pro Glu Gln Val Val Ala Ile Ala Ser His Asp Gly Gly Lys
            435                 440                 445
Gln Ala Leu Glu Thr Val Gln Arg Leu Leu Pro Val Leu Cys Gln Ala
            450                 455                 460
His Gly Leu Thr Pro Glu Gln Val Val Ala Ile Ala Ser His Asp Gly
465                 470                 475                 480
```

```
Gly Lys Gln Ala Leu Glu Thr Val Gln Arg Leu Leu Pro Val Leu Cys
                485                 490                 495
Gln Ala His Gly Leu Thr Pro Glu Gln Val Val Ala Ile Ala Ser Asn
            500                 505                 510
Ile Gly Gly Lys Gln Ala Leu Glu Thr Val Gln Ala Leu Leu Pro Val
        515                 520                 525
Leu Cys Gln Ala His Gly Leu Thr Pro Glu Gln Val Val Ala Ile Ala
    530                 535                 540
Ser His Asp Gly Gly Lys Gln Ala Leu Glu Thr Val Gln Arg Leu Leu
545                 550                 555                 560
Pro Val Leu Cys Gln Ala His Gly Leu Thr Pro Glu Gln Val Val Ala
                565                 570                 575
Ile Ala Ser His Asp Gly Gly Lys Gln Ala Leu Glu Thr Val Gln Arg
            580                 585                 590
Leu Leu Pro Val Leu Cys Gln Ala His Gly Leu Thr Pro Gln Gln Val
        595                 600                 605
Val Ala Ile Ala Ser Asn Gly Gly Lys Gln Ala Leu Glu Thr Val
    610                 615                 620
Gln Arg Leu Leu Pro Val Leu Cys Gln Ala His Gly Leu Thr Pro Gln
625                 630                 635                 640
Gln Val Val Ala Ile Ala Ser Asn Asn Gly Gly Lys Gln Ala Leu Glu
                645                 650                 655
Thr Val Gln Arg Leu Leu Pro Val Leu Cys Gln Ala His Gly Leu Thr
            660                 665                 670
Pro Gln Gln Val Val Ala Ile Ala Ser Asn Gly Gly Arg Pro Ala
        675                 680                 685
Leu Glu Ser Ile Val Ala Gln Leu Ser Arg Pro Asp Pro Ala Leu Ala
    690                 695                 700
Ala Leu Thr Asn Asp His Leu Val Ala Leu Ala Cys Leu Gly Gly Arg
705                 710                 715                 720
Pro Ala Leu Asp Ala Val Lys Lys Gly Leu Gly Asp Pro Ile Ser Arg
                725                 730                 735
Ser Gln Leu Val Lys Ser Glu Leu Glu Glu Lys Lys Ser Glu Leu Arg
            740                 745                 750
His Lys Leu Lys Tyr Val Pro His Glu Tyr Ile Glu Leu Ile Glu Ile
        755                 760                 765
Ala Arg Asn Ser Thr Gln Asp Arg Ile Leu Glu Met Lys Val Met Glu
    770                 775                 780
Phe Phe Met Lys Val Tyr Gly Tyr Arg Gly Lys His Leu Gly Gly Ser
785                 790                 795                 800
Arg Lys Pro Asp Gly Ala Ile Tyr Thr Val Gly Ser Pro Ile Asp Tyr
                805                 810                 815
Gly Val Ile Val Asp Thr Lys Ala Tyr Ser Gly Gly Tyr Asn Leu Pro
            820                 825                 830
Ile Gly Gln Ala Asp Glu Met Gln Arg Tyr Val Glu Asn Gln Thr
        835                 840                 845
Arg Asn Lys His Ile Asn Pro Asn Glu Trp Trp Lys Val Tyr Pro Ser
850                 855                 860
Ser Val Thr Glu Phe Lys Phe Leu Phe Val Ser Gly His Phe Lys Gly
865                 870                 875                 880
Asn Tyr Lys Ala Gln Leu Thr Arg Leu Asn His Ile Thr Asn Cys Asn
                885                 890                 895
```

-continued

```
Gly Ala Val Leu Ser Val Glu Glu Leu Ile Gly Glu Met Ile
                900             905             910

Lys Ala Gly Thr Leu Thr Leu Glu Glu Val Arg Arg Lys Phe Asn Asn
                915             920             925

Gly Glu Ile Asn Phe Ala Ala Asp
    930             935
```

<210> SEQ ID NO 7
<211> LENGTH: 942
<212> TYPE: PRT
<213> ORGANISM: Artificial Sequence
<220> FEATURE:
<223> OTHER INFORMATION: Laboratory-created sequence.

<400> SEQUENCE: 7

```
Met Gly Asp Pro Lys Lys Arg Lys Val Ile Asp Lys Glu Thr Ala
1               5               10              15

Ala Ala Lys Phe Glu Arg Gln His Met Asp Ser Ile Asp Ile Ala Asp
                20              25              30

Leu Arg Thr Leu Gly Tyr Ser Gln Gln Gln Gln Glu Lys Ile Lys Pro
                35              40              45

Lys Val Arg Ser Thr Val Ala Gln His His Glu Ala Leu Val Gly His
    50              55              60

Gly Phe Thr His Ala His Ile Val Ala Leu Ser Gln His Pro Ala Ala
65              70              75              80

Leu Gly Thr Val Ala Val Lys Tyr Gln Asp Met Ile Ala Ala Leu Pro
                85              90              95

Glu Ala Thr His Glu Ala Ile Val Gly Val Gly Lys Gln Trp Ser Gly
                100             105             110

Ala Arg Ala Leu Glu Ala Leu Leu Thr Val Ala Gly Glu Leu Arg Gly
                115             120             125

Pro Pro Leu Gln Leu Asp Thr Gly Gln Leu Leu Lys Ile Ala Lys Arg
                130             135             140

Gly Gly Val Thr Ala Val Glu Ala Val His Ala Trp Arg Asn Ala Leu
145             150             155             160

Thr Gly Ala Pro Leu Asn Leu Thr Pro Gln Gln Val Val Ala Ile Ala
                165             170             175

Ser Asn Asn Gly Gly Lys Gln Ala Leu Glu Thr Val Gln Arg Leu Leu
                180             185             190

Pro Val Leu Cys Gln Ala His Gly Leu Thr Pro Glu Gln Val Val Ala
                195             200             205

Ile Ala Ser Asn Ile Gly Gly Lys Gln Ala Leu Glu Thr Val Gln Ala
                210             215             220

Leu Leu Pro Val Leu Cys Gln Ala His Gly Leu Thr Pro Gln Gln Val
225             230             235             240

Val Ala Ile Ala Ser Asn Asn Gly Gly Lys Gln Ala Leu Glu Thr Val
                245             250             255

Gln Arg Leu Leu Pro Val Leu Cys Gln Ala His Gly Leu Thr Pro Gln
                260             265             270

Gln Val Val Ala Ile Ala Ser Asn Asn Gly Gly Lys Gln Ala Leu Glu
                275             280             285

Thr Val Gln Arg Leu Leu Pro Val Leu Cys Gln Ala His Gly Leu Thr
                290             295             300

Pro Glu Gln Val Val Ala Ile Ala Ser His Asp Gly Gly Lys Gln Ala
305             310             315             320
```

-continued

Leu Glu Thr Val Gln Arg Leu Leu Pro Val Leu Cys Gln Ala His Gly
                325                 330                 335

Leu Thr Pro Glu Gln Val Val Ala Ile Ala Ser Asn Ile Gly Gly Lys
            340                 345                 350

Gln Ala Leu Glu Thr Val Gln Ala Leu Leu Pro Val Leu Cys Gln Ala
        355                 360                 365

His Gly Leu Thr Pro Glu Gln Val Val Ala Ile Ala Ser His Asp Gly
    370                 375                 380

Gly Lys Gln Ala Leu Glu Thr Val Gln Arg Leu Leu Pro Val Leu Cys
385                 390                 395                 400

Gln Ala His Gly Leu Thr Pro Gln Gln Val Val Ala Ile Ala Ser Asn
            405                 410                 415

Asn Gly Gly Lys Gln Ala Leu Glu Thr Val Gln Arg Leu Leu Pro Val
        420                 425                 430

Leu Cys Gln Ala His Gly Leu Thr Pro Gln Gln Val Val Ala Ile Ala
    435                 440                 445

Ser Asn Asn Gly Gly Lys Gln Ala Leu Glu Thr Val Gln Arg Leu Leu
    450                 455                 460

Pro Val Leu Cys Gln Ala His Gly Leu Thr Pro Gln Gln Val Val Ala
465                 470                 475                 480

Ile Ala Ser Asn Asn Gly Gly Lys Gln Ala Leu Glu Thr Val Gln Arg
            485                 490                 495

Leu Leu Pro Val Leu Cys Gln Ala His Gly Leu Thr Pro Gln Gln Val
        500                 505                 510

Val Ala Ile Ala Ser Asn Asn Gly Gly Lys Gln Ala Leu Glu Thr Val
    515                 520                 525

Gln Arg Leu Leu Pro Val Leu Cys Gln Ala His Gly Leu Thr Pro Glu
530                 535                 540

Gln Val Val Ala Ile Ala Ser His Asp Gly Gly Lys Gln Ala Leu Glu
545                 550                 555                 560

Thr Val Gln Arg Leu Leu Pro Val Leu Cys Gln Ala His Gly Leu Thr
            565                 570                 575

Pro Gln Gln Val Val Ala Ile Ala Ser Asn Gly Gly Gly Lys Gln Ala
        580                 585                 590

Leu Glu Thr Val Gln Arg Leu Leu Pro Val Leu Cys Gln Ala His Gly
    595                 600                 605

Leu Thr Pro Glu Gln Val Val Ala Ile Ala Ser Asn Ile Gly Gly Lys
    610                 615                 620

Gln Ala Leu Glu Thr Val Gln Ala Leu Leu Pro Val Leu Cys Gln Ala
625                 630                 635                 640

His Gly Leu Thr Pro Gln Gln Val Val Ala Ile Ala Ser Asn Asn Gly
            645                 650                 655

Gly Lys Gln Ala Leu Glu Thr Val Gln Arg Leu Leu Pro Val Leu Cys
        660                 665                 670

Gln Ala His Gly Leu Thr Pro Gln Gln Val Val Ala Ile Ala Ser Asn
    675                 680                 685

Gly Gly Gly Arg Pro Ala Leu Glu Ser Ile Val Ala Gln Leu Ser Arg
    690                 695                 700

Pro Asp Pro Ala Leu Ala Ala Leu Thr Asn Asp His Leu Val Ala Leu
705                 710                 715                 720

Ala Cys Leu Gly Gly Arg Pro Ala Leu Asp Ala Val Lys Lys Gly Leu
            725                 730                 735

Gly Asp Pro Ile Ser Arg Ser Gln Leu Val Lys Ser Glu Leu Glu Glu

```
                      740                 745                 750
Lys Lys Ser Glu Leu Arg His Lys Leu Lys Tyr Val Pro His Glu Tyr
        755                 760                 765
Ile Glu Leu Ile Glu Ile Ala Arg Asn Ser Thr Gln Asp Arg Ile Leu
    770                 775                 780
Glu Met Lys Val Met Glu Phe Phe Met Lys Val Tyr Gly Tyr Arg Gly
785                 790                 795                 800
Lys His Leu Gly Gly Ser Arg Lys Pro Asp Gly Ala Ile Tyr Thr Val
                805                 810                 815
Gly Ser Pro Ile Asp Tyr Gly Val Ile Val Asp Thr Lys Ala Tyr Ser
            820                 825                 830
Gly Gly Tyr Asn Leu Pro Ile Gly Gln Ala Asp Glu Met Gln Arg Tyr
        835                 840                 845
Val Glu Glu Asn Gln Thr Arg Asn Lys His Ile Asn Pro Asn Glu Trp
    850                 855                 860
Trp Lys Val Tyr Pro Ser Ser Val Thr Glu Phe Lys Phe Leu Phe Val
865                 870                 875                 880
Ser Gly His Phe Lys Gly Asn Tyr Lys Ala Gln Leu Thr Arg Leu Asn
                885                 890                 895
His Ile Thr Asn Cys Asn Gly Ala Val Leu Ser Val Glu Glu Leu Leu
            900                 905                 910
Ile Gly Gly Glu Met Ile Lys Ala Gly Thr Leu Thr Leu Glu Glu Val
        915                 920                 925
Arg Arg Lys Phe Asn Asn Gly Glu Ile Asn Phe Ala Ala Asp
    930                 935                 940

<210> SEQ ID NO 8
<211> LENGTH: 17
<212> TYPE: PRT
<213> ORGANISM: Artificial Sequence
<220> FEATURE:
<223> OTHER INFORMATION: Laboratory-created sequence.

<400> SEQUENCE: 8

Asp Arg Gln Ile Lys Ile Trp Phe Gln Asn Arg Arg Met Lys Trp Lys
1               5                   10                  15
Lys

<210> SEQ ID NO 9
<211> LENGTH: 5
<212> TYPE: PRT
<213> ORGANISM: Homo sapiens

<400> SEQUENCE: 9

Ala Arg Thr Lys Gln
1               5

<210> SEQ ID NO 10
<211> LENGTH: 10
<212> TYPE: PRT
<213> ORGANISM: Homo sapiens

<400> SEQUENCE: 10

Ala Arg Thr Lys Gln Thr Ala Arg Lys Ser
1               5                   10

<210> SEQ ID NO 11
<211> LENGTH: 15
<212> TYPE: PRT
```

```
<213> ORGANISM: Homo sapiens

<400> SEQUENCE: 11

Ala Arg Thr Lys Gln Thr Ala Arg Lys Ser Thr Gly Gly Lys Ala
1               5                   10                  15

<210> SEQ ID NO 12
<211> LENGTH: 20
<212> TYPE: PRT
<213> ORGANISM: Homo sapiens

<400> SEQUENCE: 12

Ala Arg Thr Lys Gln Thr Ala Arg Lys Ser Thr Gly Gly Lys Ala Pro
1               5                   10                  15

Arg Lys Gln Leu
            20

<210> SEQ ID NO 13
<211> LENGTH: 25
<212> TYPE: PRT
<213> ORGANISM: Homo sapiens

<400> SEQUENCE: 13

Ala Arg Thr Lys Gln Thr Ala Arg Lys Ser Thr Gly Gly Lys Ala Pro
1               5                   10                  15

Arg Lys Gln Leu Ala Thr Lys Ala Ala
            20                  25
```